United States Patent
Whitfield, Sr. et al.

(10) Patent No.: US 10,252,867 B2
(45) Date of Patent: Apr. 9, 2019

(54) PALLET POSITIONING STATION AND ASSOCIATED METHODS

(71) Applicant: CHEP Technology Pty Limited, Sydney (AU)

(72) Inventors: Dwight Bryan Whitfield, Sr., Whigham, GA (US); Paul Barnswell, Debary, FL (US); James Koonce, Belle Isle, FL (US); Matthew Wood, Davenport, FL (US); Mohammad Ansari, Windermere, FL (US)

(73) Assignee: CHEP Technology Pty Limited, Sydney (AU)

( * ) Notice: Subject to any disclaimer, the term of this patent is extended or adjusted under 35 U.S.C. 154(b) by 0 days.

(21) Appl. No.: 15/656,159

(22) Filed: Jul. 21, 2017

(65) Prior Publication Data

US 2019/0023497 A1    Jan. 24, 2019

(51) Int. Cl.

| | |
|---|---|
| *B65G 47/82* | (2006.01) |
| *B65G 13/00* | (2006.01) |
| *G01N 3/30* | (2006.01) |
| *B65G 43/00* | (2006.01) |
| *B65D 19/38* | (2006.01) |

(52) U.S. Cl.
CPC .............. *B65G 47/82* (2013.01); *B65G 13/00* (2013.01); *B65G 43/00* (2013.01); *G01N 3/30* (2013.01); *B65D 19/38* (2013.01); *G01N 2203/0206* (2013.01)

(58) Field of Classification Search
CPC .................. B65G 47/82; B65G 25/08

USPC .......... 198/345.3, 743; 414/222.01
See application file for complete search history.

(56) References Cited

U.S. PATENT DOCUMENTS

| | | | | |
|---|---|---|---|---|
| 1,912,898 A | * | 6/1933 | Jennings | B65G 47/29 198/463.2 |
| 2,756,870 A | * | 7/1956 | Clark | B65B 27/06 198/721 |

(Continued)

FOREIGN PATENT DOCUMENTS

| | | |
|---|---|---|
| CN | 104833596 | 8/2015 |
| DE | 9400809 | 5/1994 |

*Primary Examiner* — Joseph A Dillon, Jr.
(74) *Attorney, Agent, or Firm* — Allen, Dyer, Doppelt & Gilchrist, P.A.

(57) ABSTRACT

A pallet positioning station for positioning a pallet on a roller conveyor to be impacted by a pallet impact station includes a frame adjacent the roller conveyor, and a pallet lift assembly carried by the frame and positioned below the roller conveyor. The pallet lift assembly includes a lift grate moveable between a retracted position and an extended position. A pallet push arm assembly is carried by the frame and includes a pallet push arm movable between a retracted position and a pallet positioning position. A controller is configured to move the pallet push arm and the lift grate to the retracted positions to receive the pallet for positioning, and move the lift grate to the extended position when the pallet is to be positioned for impact by the pallet impact station, with the pallet being lifted off of the roller conveyor by the lift grate. The controller is further configured to move the pallet push arm to the pallet positioning position to move the pallet towards the pallet impact station until an impact side of the pallet is aligned with an impact reference plane.

18 Claims, 22 Drawing Sheets

(56) References Cited

U.S. PATENT DOCUMENTS

| | | | | |
|---|---|---|---|---|
| 2,857,036 A * | 10/1958 | Leiser | ............. | B65G 25/08 |
| | | | | 198/463.3 |
| 4,214,848 A * | 7/1980 | Verwey | ............. | B65G 57/245 |
| | | | | 198/475.1 |
| 4,290,517 A * | 9/1981 | Hafferkamp | ............. | C03B 35/10 |
| | | | | 198/427 |
| 4,405,186 A * | 9/1983 | Sandberg | ............. | B26D 7/32 |
| | | | | 271/218 |
| 4,753,335 A * | 6/1988 | Goater | ............. | B65G 47/244 |
| | | | | 198/456 |
| 5,899,653 A * | 5/1999 | Brodine | ............. | H01L 21/67748 |
| | | | | 414/222.04 |
| 5,966,798 A * | 10/1999 | Ohnishi | ............. | B23D 47/042 |
| | | | | 198/345.3 |
| 6,019,211 A * | 2/2000 | Masciarelli, Jr. | ............. | B65G 13/065 |
| | | | | 193/35 MD |
| 6,053,695 A * | 4/2000 | Longoria | ............. | A21C 9/086 |
| | | | | 414/788.9 |
| 6,095,317 A * | 8/2000 | Waldner | ............. | B65G 47/642 |
| | | | | 198/463.2 |
| 6,343,906 B1 * | 2/2002 | Kraemer | ............. | G01N 35/028 |
| | | | | 198/345.3 |
| 6,516,937 B1 * | 2/2003 | Deer | ............. | B65G 43/00 |
| | | | | 198/370.07 |
| 6,681,916 B2 * | 1/2004 | Hiroki | ............. | B65G 35/06 |
| | | | | 198/347.1 |
| 6,845,860 B1 * | 1/2005 | Walker | ............. | B65G 47/53 |
| | | | | 198/433 |
| 7,275,635 B2 * | 10/2007 | Enya | ............. | B65G 37/02 |
| | | | | 198/463.2 |
| 7,287,636 B2 * | 10/2007 | Itoh | ............. | B65G 23/08 |
| | | | | 198/370.1 |
| 7,793,771 B2 * | 9/2010 | Thues | ............. | B21B 39/004 |
| | | | | 198/370.01 |
| 8,061,500 B2 * | 11/2011 | Baccini | ............. | H01L 21/681 |
| | | | | 198/345.1 |
| 8,496,102 B2 * | 7/2013 | Schaferling | ............. | B26D 7/0625 |
| | | | | 198/418.7 |
| 8,678,175 B2 * | 3/2014 | Heim | ............. | B65B 61/28 |
| | | | | 198/602 |
| 9,376,268 B2 * | 6/2016 | Schiavina | ............. | B65G 43/08 |
| 2002/0104210 A1 | 8/2002 | Buck | | |
| 2006/0174719 A1 | 8/2006 | Carter et al. | | |
| 2006/0242820 A1 | 11/2006 | Townsend et al. | | |
| 2006/0283687 A1 * | 12/2006 | Heinemeier | ............. | B62D 65/18 |
| | | | | 198/345.3 |
| 2014/0046810 A1 | 2/2014 | Stevens | | |
| 2014/0102338 A1 | 4/2014 | Stevens | | |
| 2015/0175371 A1 * | 6/2015 | Dim | ............. | B65H 3/44 |
| | | | | 427/256 |
| 2015/0306714 A1 | 10/2015 | Rahman et al. | | |
| 2015/0360809 A1 | 12/2015 | McBride et al. | | |
| 2015/0368048 A1 * | 12/2015 | Benz | ............. | B65G 47/34 |
| | | | | 414/222.01 |

\* cited by examiner

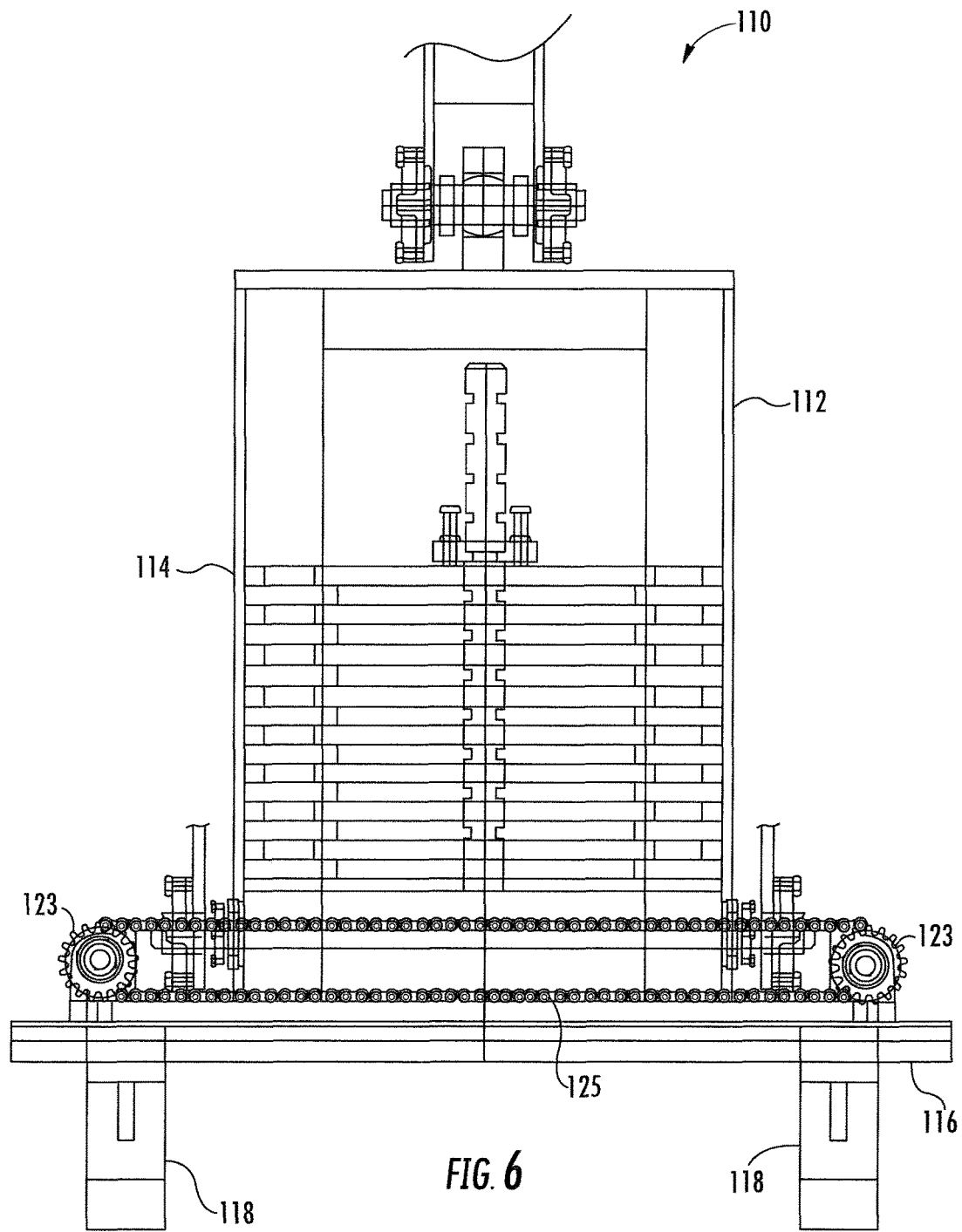

PALLET POSITIONING STATION AND ASSOCIATED METHODS

FIELD OF THE INVENTION

The present invention relates to the field of pallets, and more particularly, to a pallet positioning system for use with a pallet impact station.

BACKGROUND OF THE INVENTION

Wooden pallets are used to transport a variety of bulk goods and equipment as required in manufacturing and warehousing operations. In high volume industries, pallet pools provide a lower total industry cost than one-way pallets. The current assignee of the present invention recognizes the benefits of pooled pallets, and currently has over several hundred million pallets that are pooled each year.

Conventional wood pallets include a base layer and a cargo layer separated therefrom by support blocks. The support blocks form a gap between the base and cargo layers for receiving a lifting member. Traditionally, the base and cargo layers respectively have end deck boards assembled on connector boards that run the full length or width of the pallet.

As one might expect, wooden pallets are subject to damage in use that occurs from handling with forklifts or other like equipment. To move the wooden pallets with cargo thereon, forklift tines from a forklift, for example, are inserted into the gap between the base and cargo layers. If the forklift tines are not properly aligned within the gap, they may crash into the support blocks or into the end deck boards or connector boards in the base or cargo layers. Impacts such as this weaken the pallet and greatly shorten the life cycle of the pallet, thereby causing the pallet to be repaired more frequently and/or removed from service before its anticipated life cycle has been reached.

Consequently, there is a need to test the life cycle of a pallet. This is particularly helpful when design changes are being made to a pallet. If the design changes are determined to increase the life cycle of the pallet, then the redesigned pallets may be inserted into the pallet pool. The difficulty in simulating the life cycle of a pallet is to be able to repeatedly strike the pallet in a precise location with a predetermined amount of energy. In addition, if the pallet is not square prior to impact, or if the pallet is not repositioned prior to receiving another impact, then the amount of energy striking the pallet varies. This degrades the accuracy of the life cycle testing of the pallet.

SUMMARY OF THE INVENTION

A pallet positioning station for positioning a pallet on a roller conveyor to be impacted by a pallet impact station includes a frame adjacent the roller conveyor and aligned with the pallet impact station, and a pallet lift assembly carried by the frame and positioned below the roller conveyor. The pallet lift assembly may comprise a lift grate moveable between a retracted position and an extended position, with the lift grate recessed below an upper surface of the roller conveyor when in the retracted position, and with the lift grate extending above the upper surface of the roller conveyor when in the extended position. A pallet push arm assembly may be carried by the frame and includes a pallet push arm movable between a retracted position and a pallet positioning position.

A controller may be configured to move the pallet push arm and the lift grate to the retracted positions when the pallet is to be positioned, and move the lift grate to the extended position when the pallet is to be positioned for impact by the pallet impact station, with the pallet being lifted off of the roller conveyor by the lift grate. The controller may be further configured to move the pallet push arm to the pallet positioning position to move the pallet towards the pallet impact station until an impact side of the pallet is aligned with an impact reference plane.

The pallet positioning station may further comprise a movement sensor carried by the frame and configured to generate a signal corresponding to movement of the pallet push arm when in the pallet positioning position. The controller may be further configured to move the pallet push arm in the pallet positioning position until the generated signal reaches a predetermined value, with the predetermined value corresponding to when the impact side of the pallet is aligned with the impact reference plane.

The pallet positioning station is advantageously used to repeatedly position a pallet at the impact reference plane which corresponds to where the pallet impact station optimally impacts the pallet. The controller advantageously monitors movement of the pallet push arm to know when the impact side of the pallet is aligned with the impact reference plane. In addition, the pallet is impacted when lifted off of the roller conveyor to ensure that the roller conveyor will not cause a drag to be present during impact.

The controller may be further configured to move the pallet push arm back to the retracted position before the pallet is impacted by the pallet impact station.

The roller conveyor may include a plurality of spaced apart elongated rollers that are parallel to one another, and wherein the lift grate may include a plurality of spaced apart elongated lift elements, with each respective lift element sized to fit between two adjacent rollers.

The pallet lift assembly may further include a plurality of vertical actuators extending between the frame and the lift grate for moving the lift grate when activated via the controller between the retracted position and the extended position.

The pallet lift assembly may further comprise at least one horizontal actuator for moving the lift grate in a horizontal direction between the impact reference plane and the pallet push arm. The controller may be further configured to move the lift grate in the horizontal direction towards the pallet push arm so that the pallet contacts the pallet push arm before the pallet push arm is moved to the pallet positioning position.

The pallet lift assembly may further comprise a radius arm rotatably coupled to the frame, and a link extending between the radius arm and the lift grate. The at least one horizontal actuator may extend between the frame and the radius arm.

The pallet push arm assembly may comprise a pair of spaced apart radius arms rotatably coupled to the frame, a pair of spaced apart links extending between the pair of radius arms and the pallet push arm, and a pair of actuators extending between the frame and the pair of radius arms for moving the pallet when activated via the controller.

The pallet may carry a unit load during impact with the pallet impact station. The pallet impact station may comprise a stationary unit load push bar positioned above the roller conveyor and adjacent the impact reference plane. As the controller moves the pallet push arm in the pallet positioning position, the unit load contacts the stationary unit load push bar as the impact side of the pallet continues to move towards the impact reference plane.

Another aspect is directed to a method for operating a pallet positioning station as described above. The method comprises moving the pallet push arm and the lift grate to the retracted positions when the pallet is received for positioning, and moving the lift grate to the extended position when the pallet is to be positioned for impact by the pallet impact station, with the pallet being lifted off of the roller conveyor by the lift grate. The method may further comprise moving the pallet push arm to the pallet positioning position to move the pallet towards the pallet impact station until an impact side of the pallet is aligned with an impact reference plane.

BRIEF DESCRIPTION OF THE DRAWINGS

FIG. 6 is a more detailed top view of the carriage assembly illustrated in FIG. 1.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
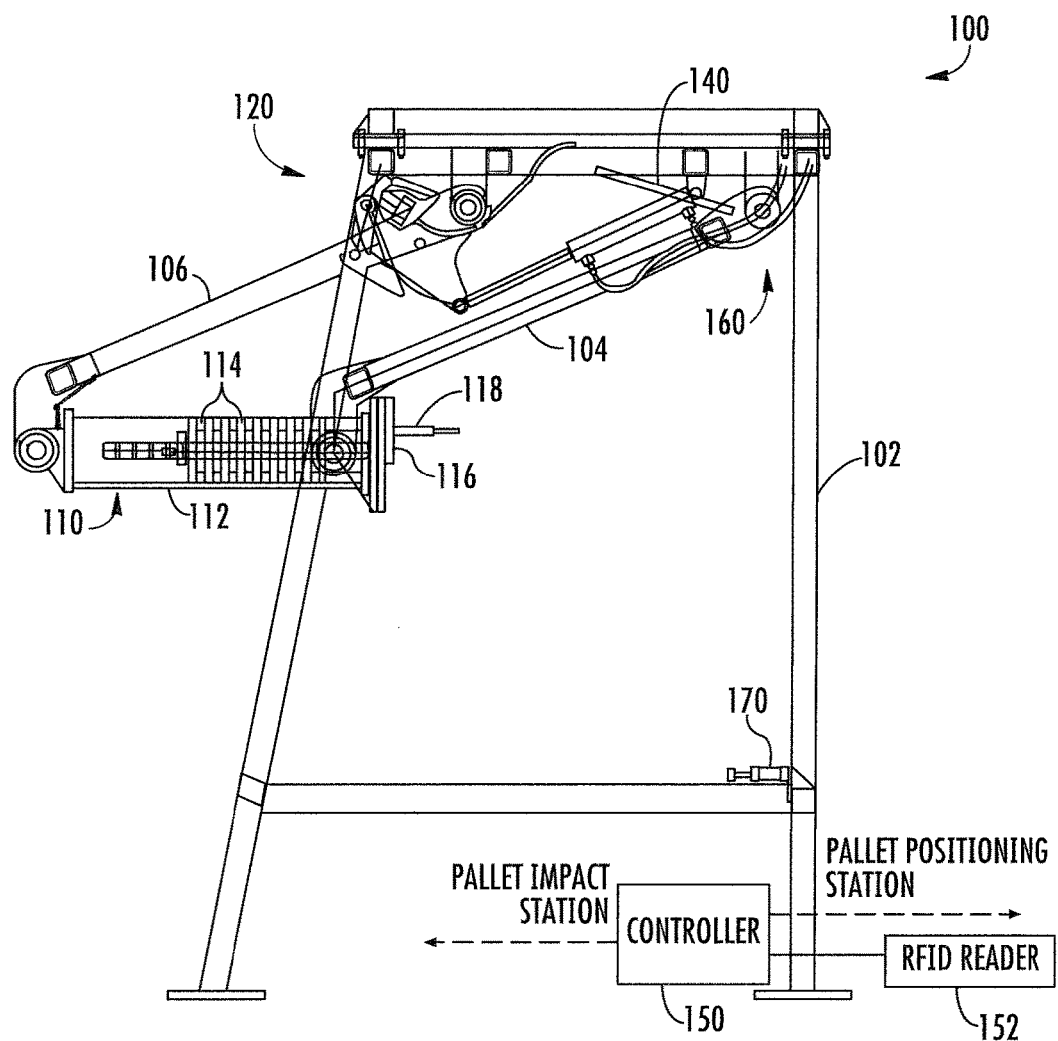
FIG. 1 is a side view of a pendulum impact station with the carriage assembly in the raised position in accordance with the present invention.
Figure 2:
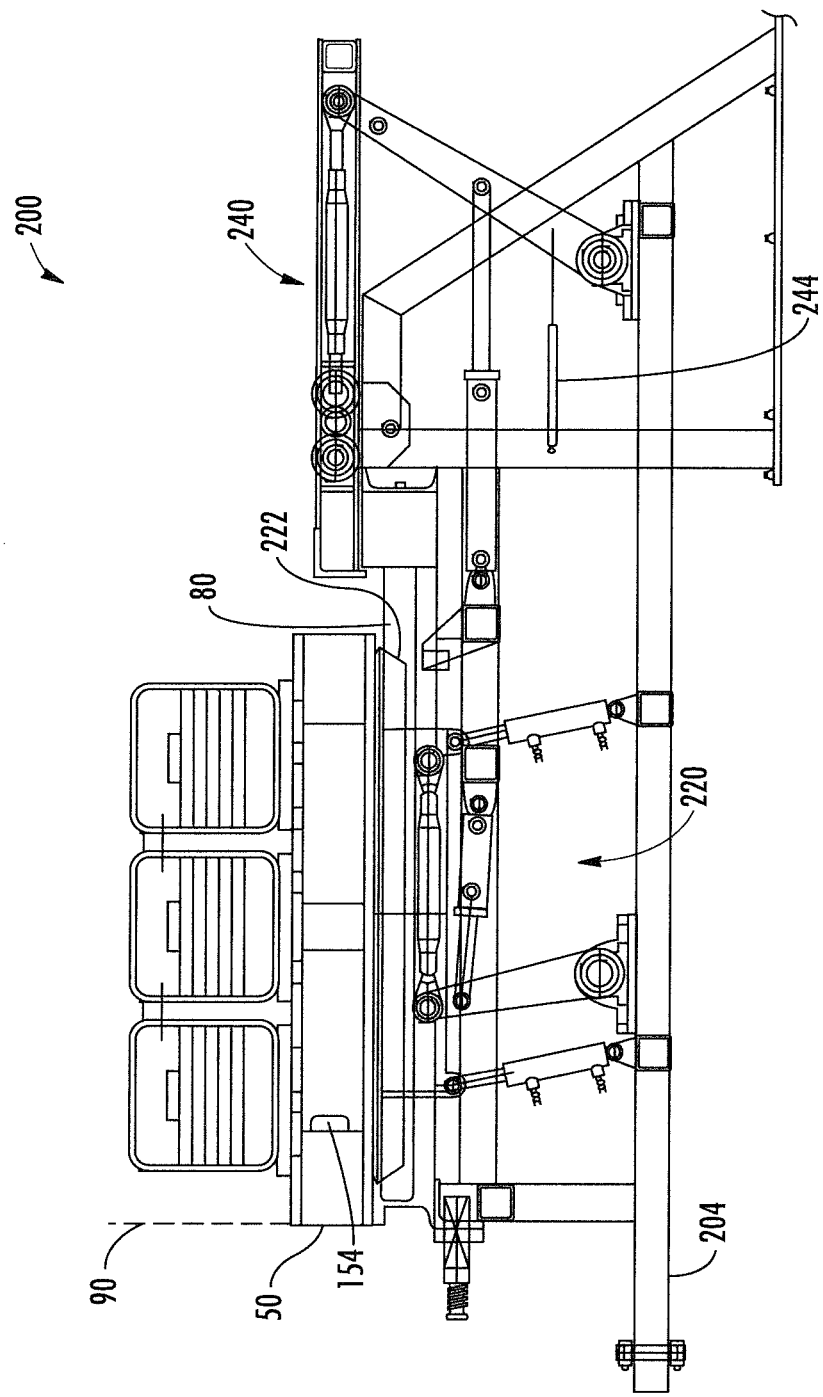
FIG. 2 is a side view of a pallet positioning station with a pallet positioned for impact in accordance with the present invention.

A life cycle pallet tester includes a pallet impact station 100 as illustrated in FIG. 1, and a pallet positioning station 200 as illustrated in FIG. 2. The pallet positioning station 200 is configured to repeatedly position a test pallet 50 at a same location on a roller conveyor 80 before each impact by the pallet impact station 100. The pallet impact station 100 is configured to impact the test pallet 50 with a programmable amount of force at a precise location after having been positioned by the pallet positioning station 200. The pallet impact station 100 will be discussed in detail first, followed by the pallet positioning station 200.

The combination of the two stations 100, 200 advantageously allows the life cycle of the test pallet 50 to be accurately evaluated and in a timely manner. A controller 150 is coupled to the pallet impact station 100 and to the pallet positioning station 200 to coordinate and synchronize operations therebetween with respect to life cycle testing of the test pallet 50.

The pallet impact station 100 includes a frame 102 and at least one pendulum swing arm rotatably coupled to the frame 102. In the illustrated embodiment, the at least one pendulum swing arm includes a front pendulum swing arm 104 and a rear pendulum swing arm 106.

A carriage assembly 110 is carried by the front and rear pendulum swing arms 104, 106. The carriage assembly 110 includes a carriage 112, a plurality of counter weights 114 carried by the carriage, and an impact plate 116 carried by the carriage 112.

A latching mechanism 120 extends between the frame 102 and one of the pendulum swing arms, such as the rear pendulum swing arm 106. The latching mechanism 120 is configured to engage the rear pendulum swing arm 106 when the carriage assembly 110 is in a lowered position, raise the carriage assembly 110 to a raised positon, and disengage the rear pendulum swing arm 106 at the raised positon so that the impact plate 116 strikes the test pallet 50 as the carriage assembly 110 falls.

A movement sensor 140 is carried by the forward pendulum swing arm 104 and is configured to generate a signal corresponding to how high the carriage assembly 110 is raised by the latching mechanism 120. More particularly, the movement sensor 140 is a linear variable differential transformer (LVDT) extending between the frame 102 and the forward pendulum swing arm 104. The controller 150 is configured to operate the latching mechanism 120, including disengaging the rear pendulum swing arm 106 when a height of the carriage assembly 110 as determined by the generated signal corresponds to a desired release height.

The pallet impact station 100 is designed to deliver an impact force between 10 and 2500 joules to the test pallet 50. Typically, an impact force between 600 to 1100 joules is applied to the test pallet 50 during a lift cycle test. The delivered impact force is based on the amount of counter weights 114 carried by the carriage assembly 110, and how high the carriage assembly 110 is raised before being released. The carriage assembly 110 may be raised up to 60 degrees, for example.

Each counter weight 114 carried by the carriage 112 weighs 50 pounds, for example. The carriage 112 is sized to carry up to 12 counter weights 114. Counter weights 114 are manually added or removed as necessary in support of the impact forces to be delivered to the test pallet 50.

As noted above, the controller 150 operates the latching mechanism 120 to raise the carriage assembly 110, and to release the carriage assembly 110 at a desired release height that will deliver a desired impact force to the test pallet 50. The desired impact force is programmable in the sense that the controller 150 calculates the desired release height to deliver the desired impact force while taking into account the number of counter weights 114 in the carriage assembly 110. By changing the release height of the carriage assembly 110 the amount of the impact force delivered to the test pallet 50 likewise changes.

The controller 150 knows when the desired release height is reached by the carriage assembly 110 based on the movement sensor 140 generating a signal corresponding to how high the carriage assembly 110 is being raised by the latching mechanism 120.

One approach to providing the desired impact force to be applied to the test pallet 50 is based on the controller 150 interfacing with an RFID reader 152, which in turn reads an RFID tag 154 carried by the test pallet 50. As the test pallet 50 is moved over the roller conveyor 80 towards the pallet impact station 100, the RFID reader 152 reads the RFID tag 154. Information directed to testing of the test pallet 50 is then provided to the controller 150 by the RFID reader 152. The RFID tag 154 also helps to keep track of each individual test pallet 50 during testing.

The information on the RFID tag 154 includes the desired impact force to be applied to the test pallet 50 as well as the dimensions or size of the pallet. Dimensions of the test pallet 50 are needed for the pallet positioning station 200 to position the test pallet 50 before each impact by the carriage assembly 110. Once the controller 150 receives this information it then determines how high the carriage assembly 110 is to be raised, based on the amount of counter weights 114 currently being carried, so as to provide the desired impact force on the test pallet 50.

As an alternative to using an RFID tag 154 and an RFID reader 152 to communicate with the controller 150, the test pallet 50 may carry a bar code or QR code that is to be read by an optical reader or scanner that then communicates with the controller 150. Yet another option is to manually enter or program the controller 150 with the desired impact force to be delivered to the test pallet 50.

Figure 3:
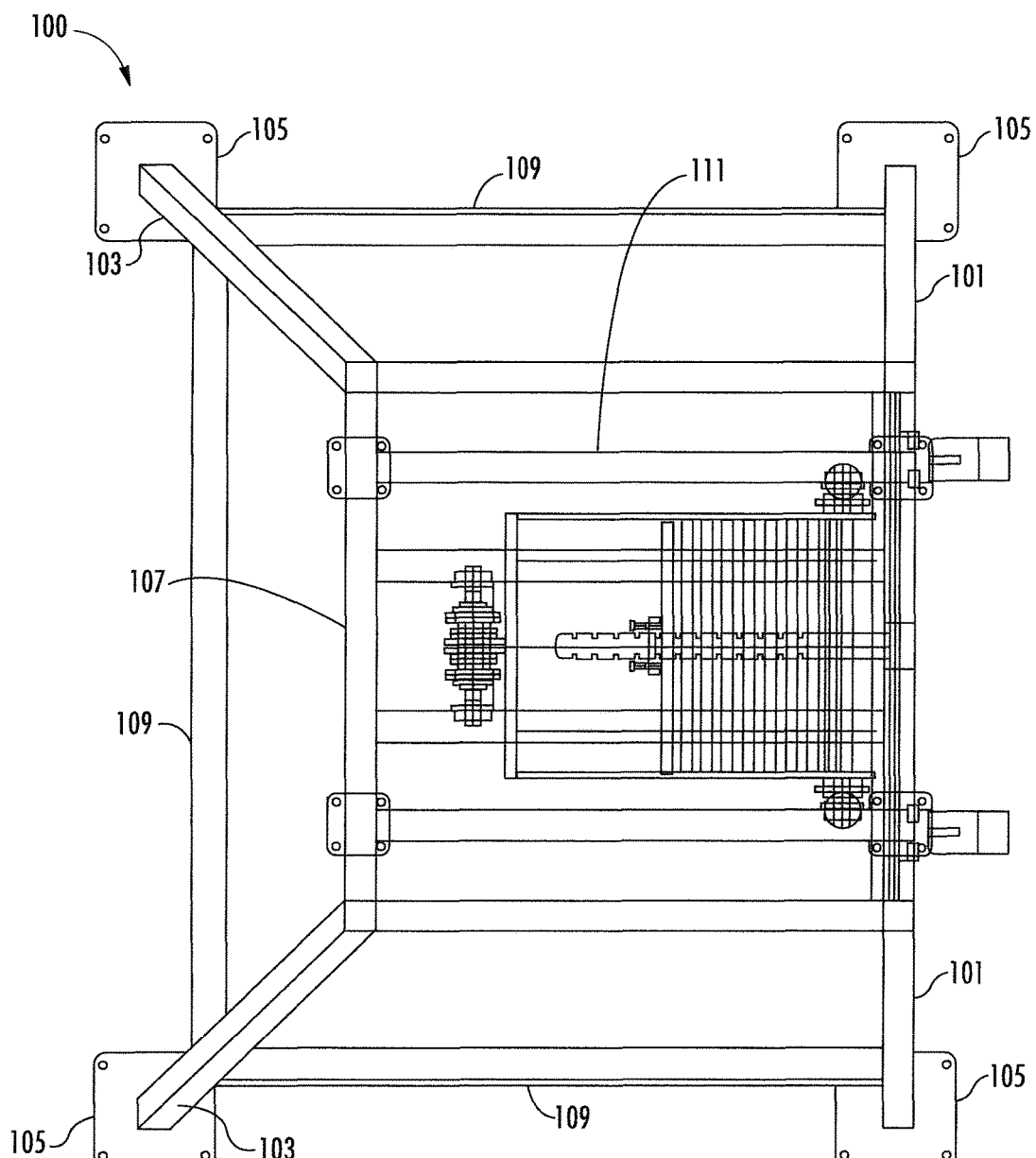
FIG. 3 is a top view of the pendulum impact station illustrated in FIG. 1.
Figure 5:
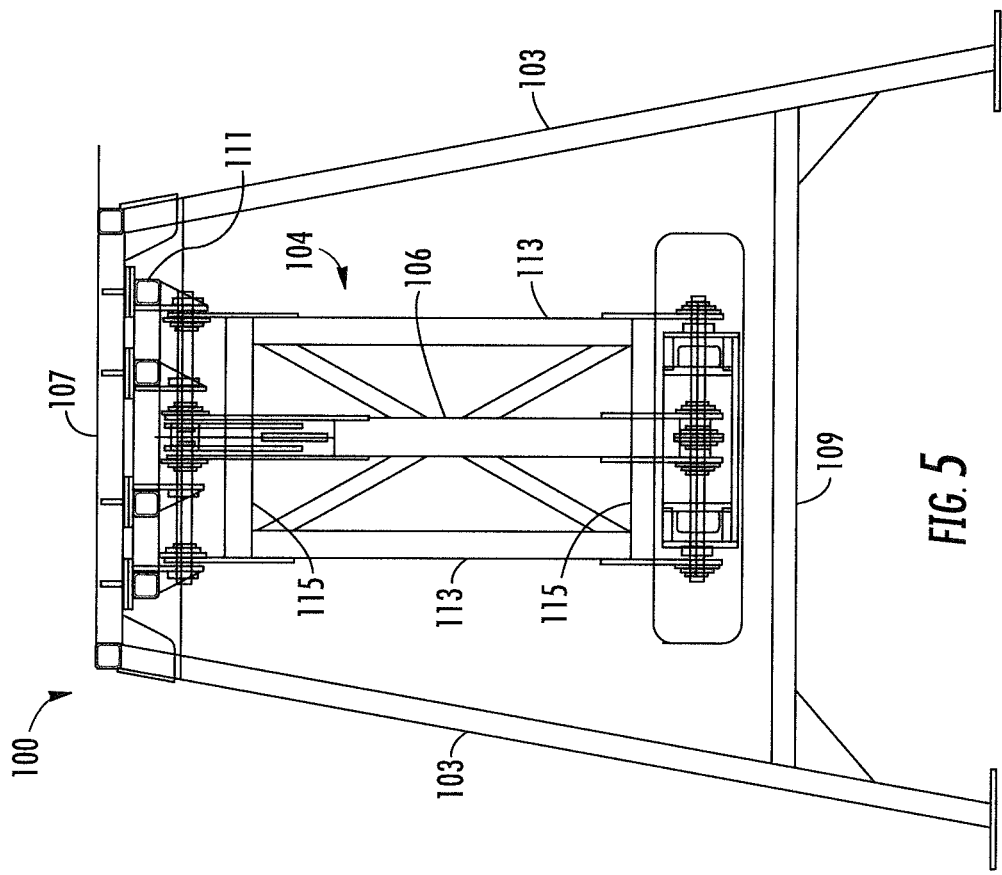
FIG. 5 is a rear view of the pendulum impact station illustrated in FIG. 4.
Figure 4:
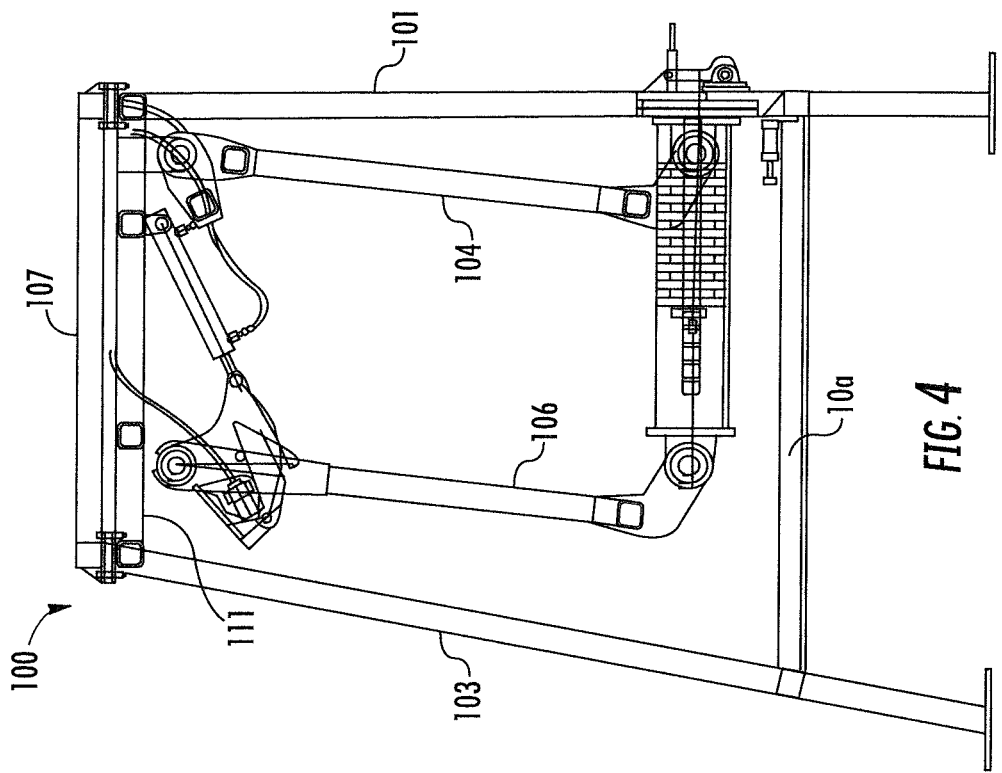
FIG. 4 is a side view of the pendulum impact station illustrated in FIG. 1 with the carriage assembly in the lowered position.

Referring now to FIGS. 3-5, the illustrated frame 102 for the pallet impact station 100 includes a pair of front legs 101 and a pair of rear legs 103 each extending from respective surface mounting plates 105 to a rectangular-shaped upper support 107. The front legs 101 are vertically positioned whereas the rear legs 103 are slightly angled or tilted towards the front legs 101. Additional side supports 109 extend between adjacent legs 101, 103.

The rectangular-shaped upper support 107 of the frame 102 further includes a pendulum swing arm sub-frame support 111 coupled thereto. The upper portion of the front and rear pendulum swing arms 104, 106 are pivotably coupled to the pendulum swing arm sub-frame support 111.

The front pendulum swing arm 104 includes a pair of spaced apart side arms 113 with upper and lower cross members 115 extending between the side arms 113. The rear pendulum swing arm 104 is a single arm.

Figure 7:
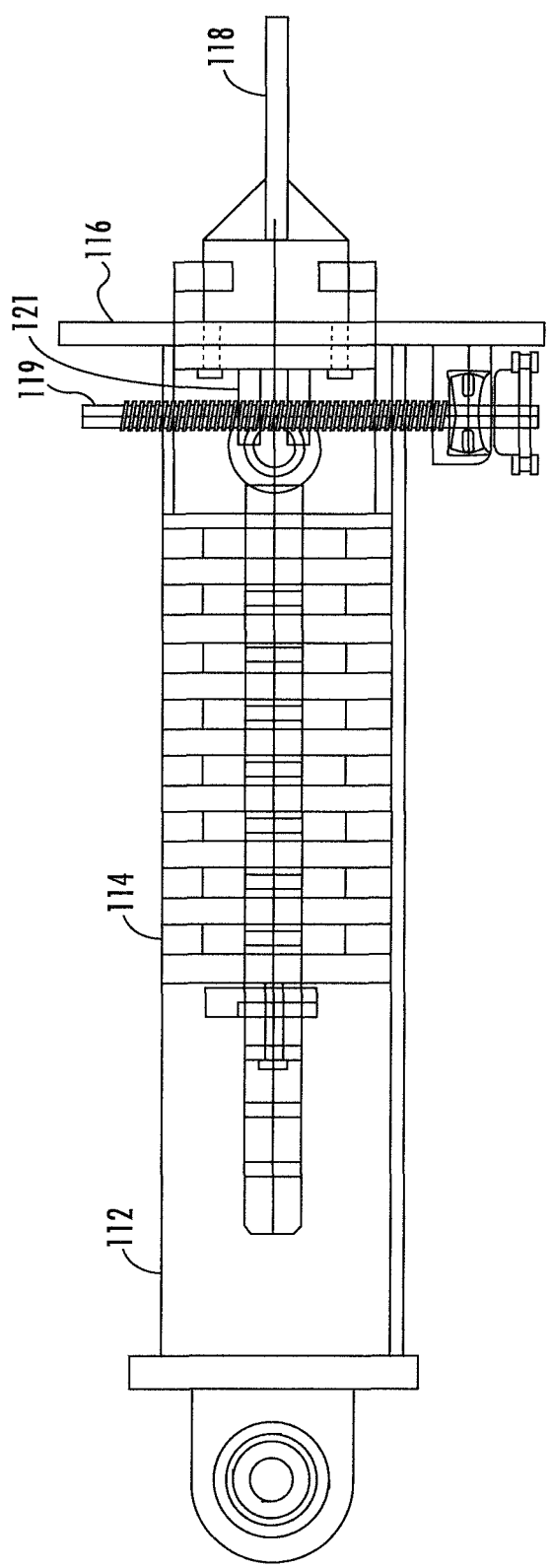
FIG. 7 is a partial side view of the carriage assembly illustrated in FIG. 6.

Referring now to FIGS. 6 and 7, the impact plate 116 carried by the carriage 112 has provisions for carrying one or more impact tines 118. In the illustrated embodiment, there is a pair of spaced apart impact tines 118. The impact tines 118 are representative of the tines on a forklift, for example. The impact tines 118 are not limited to any particular shape or size and are generally selected to be representative of the type of impact test being duplicated on the test pallet 50.

The impact plate 116 may be raised or lowered so that the impact tines 118 strike the test pallet 50 at a desired location. For example, the impact plate 116 may be positioned so that the impact tines 118 strike the support blocks of the test pallet. Alternatively, the impact plate 116 may be positioned so that the impact tines 118 strike an end deck board or connector boards on the test pallet 50.

The impact plate 116 is raised or lowered by turning a threaded shaft 119 clockwise or counter-clockwise. There are a pair of threaded shafts 119, one near each end of the impact plate 116. Each threaded shaft 119 passes through a respective threaded shaft receiving section 121 coupled to the impact plate 116.

One end of each threaded shaft 119 is coupled to a respective gear sprocket 123. A chain 125 is coupled to the spaced apart gear sprockets 123 so that when one of the threaded shafts 119 is rotated, the chain 125 will rotate the gear sprocket 123 causing the other threaded shaft 119 to likewise rotate. Although not illustrated, a crank or handle would be coupled to the other end of one of the threaded shafts 119.

The impact tines 118 may also be adjusted left and right. The face of the impact plate 116 has a keyed opening, for example, so that the impact tines 118 may be slid so that they are closer together or spaced further apart as desired.

The latching mechanism 120 will now be discussed in more detail in reference to FIGS. 8-13. More particularly, the latching mechanism 120 includes a trigger housing 122 and a trigger 124 rotatably positioned within the trigger housing. A first actuator 126 moves the trigger 124 to engage the rear pendulum swing arm 106 when activated via the controller 150 and to raise the carriage assembly 110. A second actuator 128 moves the trigger 124 to disengage the rear pendulum swing arm 106 when activated via the controller 150 so that the carriage assembly 110 falls toward the test pallet 50.

The first actuator 126 may be referred to as the carriage assembly raise actuator. The second actuator 128 may be referred to as the trigger release actuator. The first and second actuators 126, 128 are hydraulic actuators, for example, and are controlled by the controller 150.

Even though the latching mechanism 120 is coupled to the rear pendulum swing arm 106, the forward pendulum swing arm 104 is configured to move when the rear pendulum swing arm 106 moves since they are both coupled to the carriage assembly 110. As both of the pendulum swing arms 104, 106 are raised, the carriage assembly 110 is likewise raised.

Figure 8:
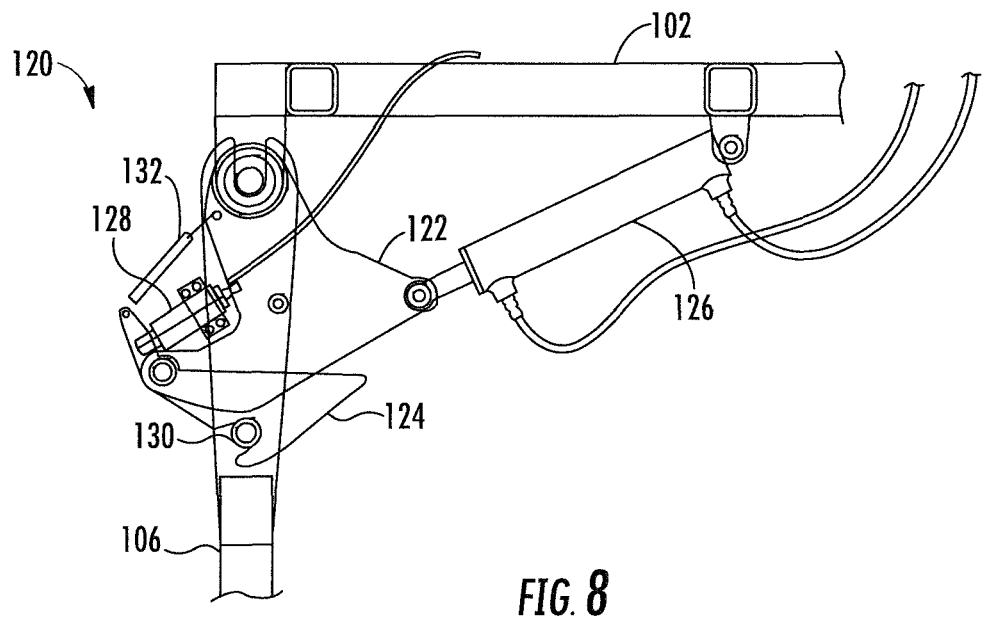
FIGS. 8-12 are side views of the latching mechanism for the carriage assembly illustrated in FIG. 1 at different positions.

For the trigger 124 to engage the rear pendulum swing arm 106, the carriage assembly 110 is in a lowered or down positon, which means that the forward and rear pendulum swing arms 104, 106 are also in the lowered or down position, as illustrated in FIG. 8. The rear pendulum swing arm 106 includes a trigger catch 130. The first actuator 126 pulls the trigger housing 122 back towards itself which in turn pulls back the trigger 124. As the trigger 124 is pulled back it slides over the trigger catch 130. The trigger 124 is pulled back until it is cleared to engage the trigger catch 130. A spring 132 extends between the trigger housing 124 and the trigger 122 to bias the trigger towards the trigger catch 130.

Figure 9:
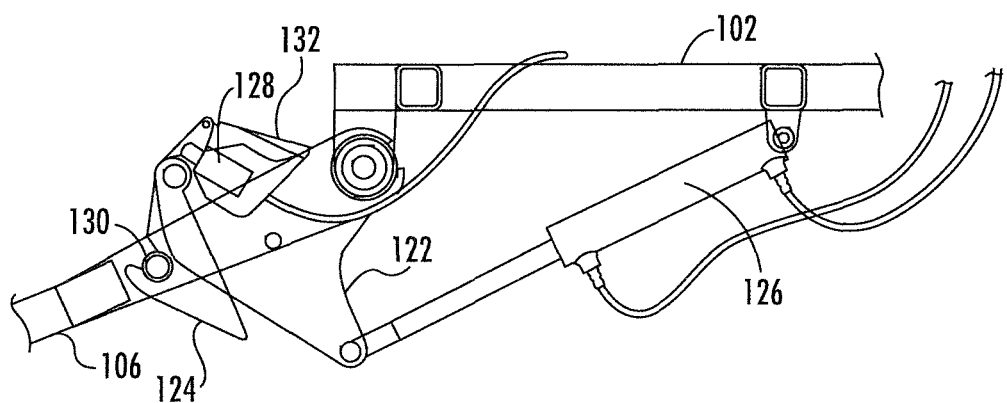

After the trigger 124 is ready to engage the trigger catch 130, the first actuator 126 pushes the trigger housing 122. Pushing the trigger housing 122 causes the trigger 124 to push against the trigger catch 130. This then causes the rear pendulum swing arm 106 to move to a raised position, as illustrated in FIG. 9.

Figure 10:
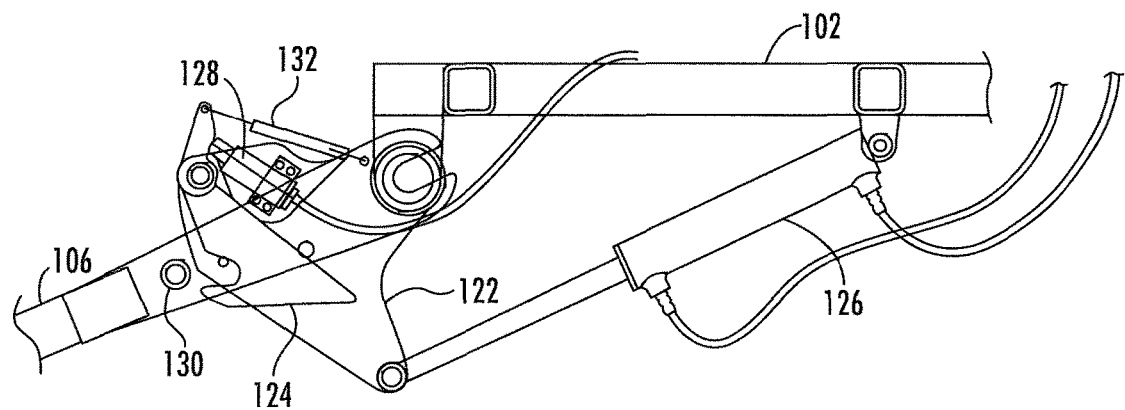

When the carriage assembly 110 is raised to a desired height, as determined by the controller 150 via the movement sensor 140, the second actuator 128 pushes the trigger 124 causing it to disengage from the trigger catch 130, as illustrated in FIG. 10. Using the second actuator 128 to release the trigger 124 allows the carriage assembly 110 to freefall to the test pallet 50.

Figure 11:
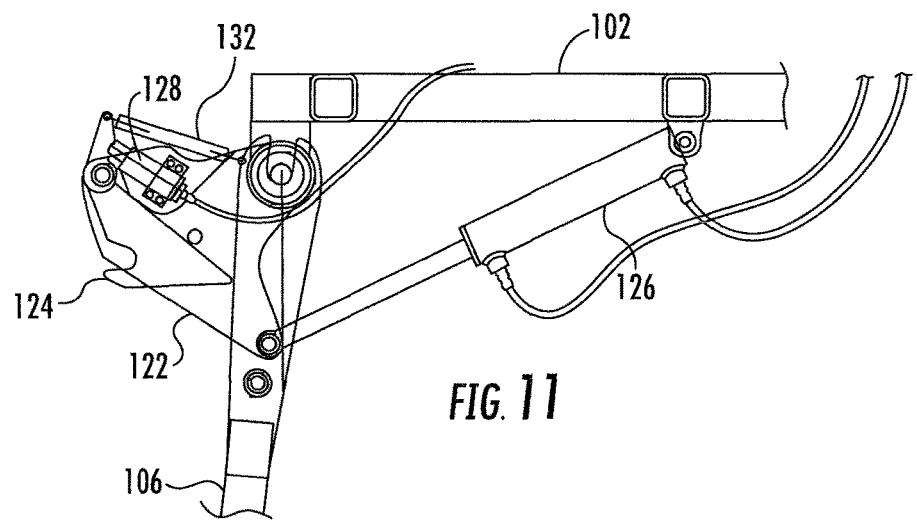

Once the trigger 124 clears the trigger catch 130, the carriage assembly 110 falls toward the test pallet 50. The forward and rear pendulum swing arms 104, 106 in turn follow the carriage assembly 110, as illustrated in FIG. 11.

The first and second actuators 126, 128 do not add any drag on the carriage assembly 110 as the carriage assembly 110 falls to the test pallet 50. The latching mechanism 120 thus allows the impact force of the carriage assembly 110 to be more accurately controlled since it is not adding drag to the carriage assembly 110.

Figure 12:
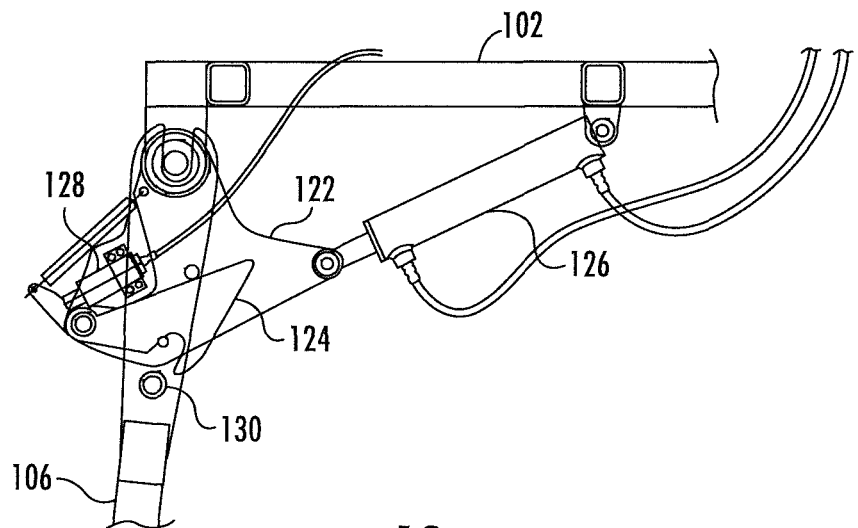

As the carriage assembly 110 is freefalling toward the test pallet 50, the latching mechanism 120 follows the carriage assembly 110, as illustrated in FIG. 12. The first actuator 126 again pulls the trigger housing 122 back towards itself which in turn pulls back the trigger 124 until it is cleared to engage the trigger catch 130 again.

Figure 13:
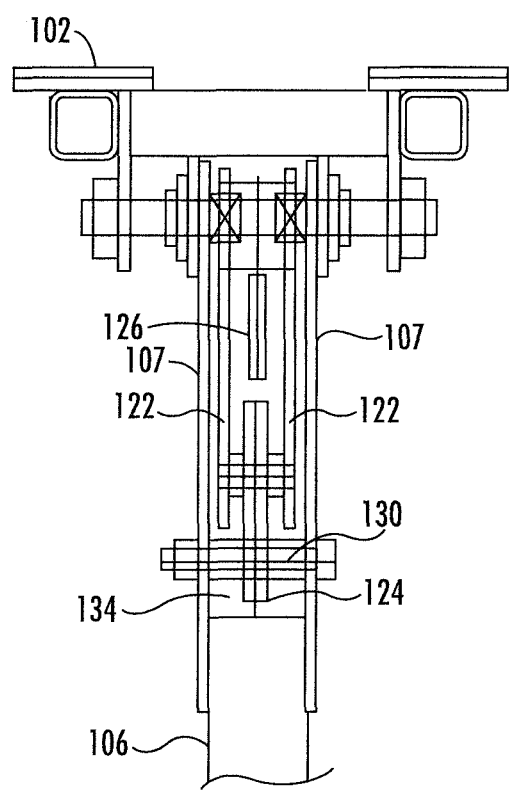
FIG. 13 is an end view of the latching mechanism illustrated in FIG. 8.

An end view of the latching mechanism 120 in FIG. 13 shows that the rear pendulum swing arm 106 includes an opening 134 for the latching mechanism 120 to move back and forth through. The trigger 124 is centered within the trigger housing 122, and the trigger catch 130 extends across the opening 134. The rear pendulum swing arm 106 includes a pair of side extensions or side plates 107 partially covering the sides of the latching mechanism 120.

Figure 14:
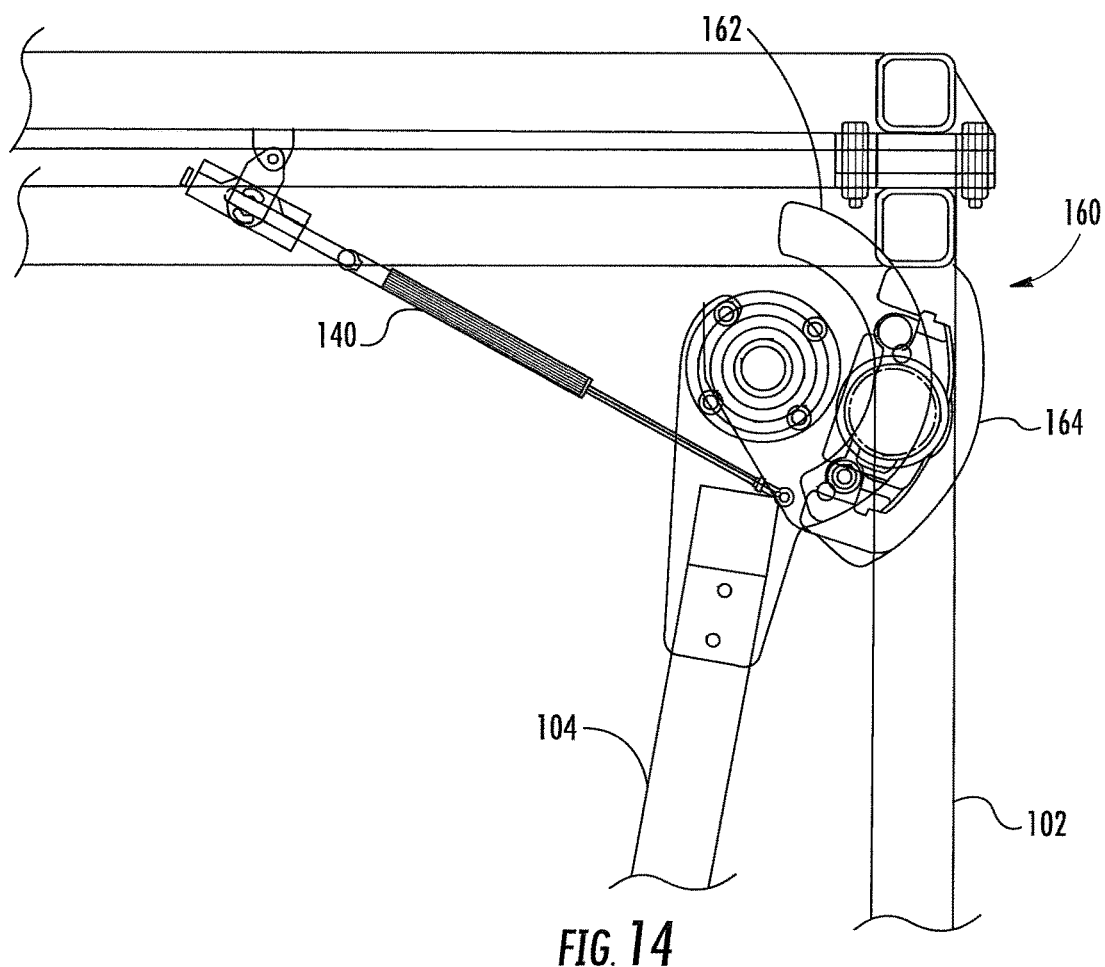
FIG. 14 is a side view of the braking mechanism for the carriage assembly illustrated in FIG. 1.
Figure 15:
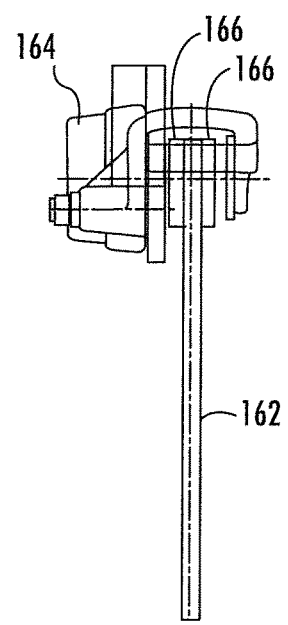
FIG. 15 is a partial end view of the braking mechanism illustrated in FIG. 14.

Referring now to FIGS. 14 and 15, the pallet impact station 100 further includes a braking mechanism 160 carried by one of the pendulum swing arms, such as the forward pendulum swing arm 104. The controller 150 momentarily activates the braking mechanism 160 after the carriage assembly 110 strikes the test pallet 50.

This is done to take the energy out of the carriage assembly 110 after impacting the test pallet 50 so as to prevent the carriage assembly 110 from bouncing back and striking the test pallet 50 again. After the braking mechanism 160 releases the forward pendulum swing arm 104, the trigger 124 from the latching mechanism 120 is moved to engage the trigger catch 130 so that the carriage assembly 110 may be raised again.

The braking mechanism 160 is configured as a disc brake commonly used on cars and trucks. The braking mechanism 160 includes a partial rotor 162 having an arc of about 120 degrees carried by the forward pendulum swing arm 104. Mounted to the frame 102 are the remaining components of the brake mechanism 160. These components include a brake caliber 164 and a pair of brake pads 166. The partial rotor 162 moves in and out of the brake caliber 164 and the pair of brake pads 166.

A proximity sensor 170 is carried by the frame 102 and is configured to generate a proximity signal when the forward pendulum swing arm 104 passes the proximity sensor prior to the carriage assembly 110 striking the pallet. The controller 150 is further configured to momentarily activate the braking mechanism 160 after a time delay from receiving the proximity signal.

The pallet positioning station 200 as illustrated in FIG. 2 will now be disused in more detail. The pallet positioning station 200 is the other half of the life cycle pallet tester, and is configured to repeatedly position the test pallet 50 at a same location on a roller conveyor 80 before each impact by the pallet impact station 100.

The pallet positioning station 200 includes a frame 204 adjacent the roller conveyor 80 and aligned with the pallet impact station 100, and a pallet lift assembly 220 carried by the frame and positioned below the roller conveyor 80.

The pallet lift assembly 220 includes a lift grate 222 moveable between a retracted position and an extended position. The lift grate 222 is recessed below an upper surface of the roller conveyor 80 when in the retracted position, and extends above the upper surface of the roller conveyor 80 when in the extended position so as to lift the test pallet 50 off of the roller conveyor 80.

A pallet push arm assembly 240 is carried by the frame 204 and includes a push arm 242 movable between a retracted position and a pallet positioning position. A movement sensor 244 is carried by the frame 204 and is configured to generate a signal corresponding to movement of the push arm 242 when in the pallet positioning position. More particularly, the movement sensor 244 is a linear variable differential transformer (LVDT) extending between the frame 204 and the pallet push arm assembly 240.

The controller 150 is configured to move the push arm 242 and the lift grate 222 to the retracted positions when the test pallet 50 is initially positioned by the roller conveyor 80 adjacent the pallet impact station 100. The controller 150 is configured to move the lift grate 222 to the extended position when the test pallet 50 is to be positioned for impact by the pallet impact station 100, with the test pallet 50 being lifted off of the roller conveyor 80.

The controller 150 is further configured to move the push arm 242 to the pallet positioning position to contact the test pallet 50 and to continue moving the test pallet 50 towards the pallet impact station 100 until an impact side of the test pallet 50 is aligned with an impact reference plane 90 based on the generated signal as provided by the movement sensor 244 reaching a predetermined value. The impact reference plane 90 may also be referred to as the zero reference plane which corresponds to when the carriage assembly 110 is in its lowermost position. The tips of the impact tines 118 contact the impact side of the test pallet 50 at the zero reference plane so as to provide delivery of an optimum impact force.

Referring now to FIGS. 16-20, the pallet lift assembly 220 will be discussed in greater detail. The illustrated pallet lift assembly 220 includes a plurality of vertical actuators 224 extending between the frame 204 and the lift grate 222 for moving the lift grate 222 when activated via the controller 150 between the retracted position and the extended position. In total there are 4 vertical actuators 224, with one adjacent each corner of the lift grate 222. The vertical actuators 224 are hydraulic actuators, for example, and are controlled by the controller 150.

Figure 16:
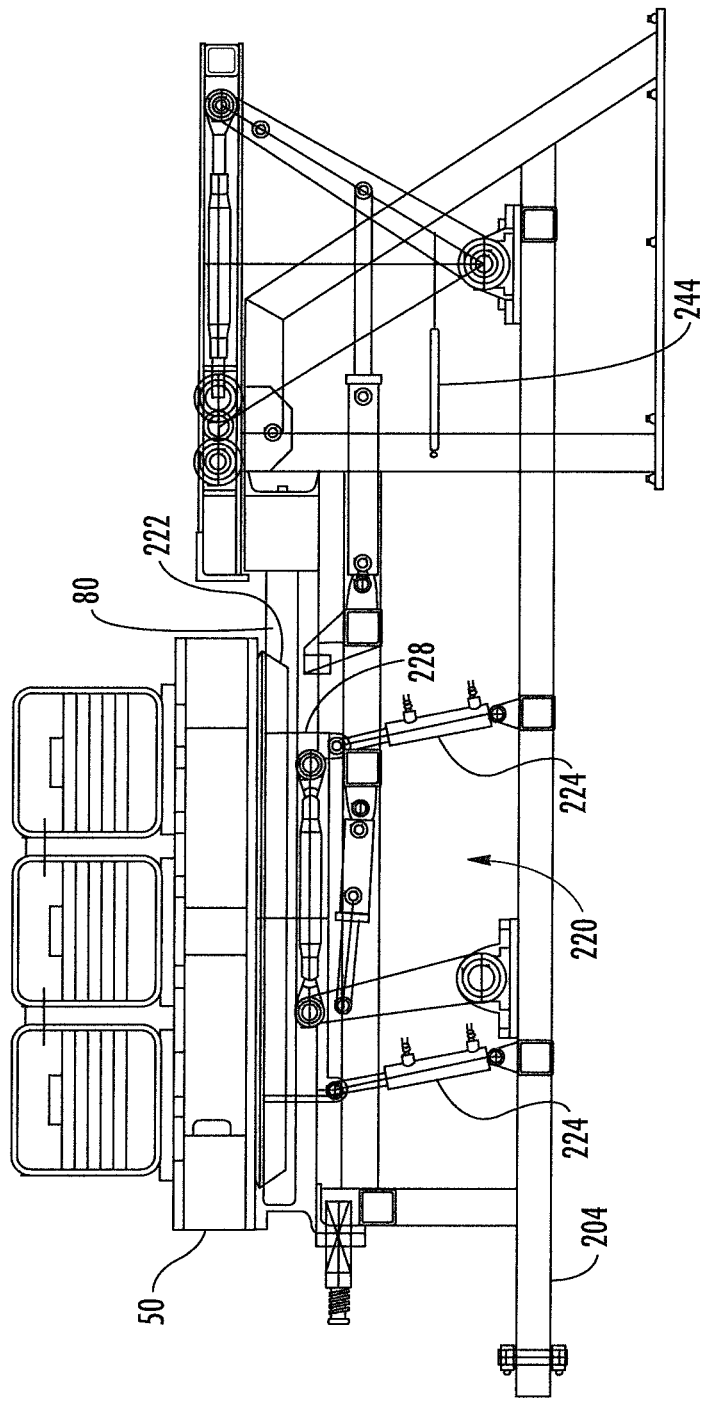
FIG. 16 is a side view of the pallet positioning station illustrated in FIG. 2 with the lifting grate in a retracted position.
Figure 17:
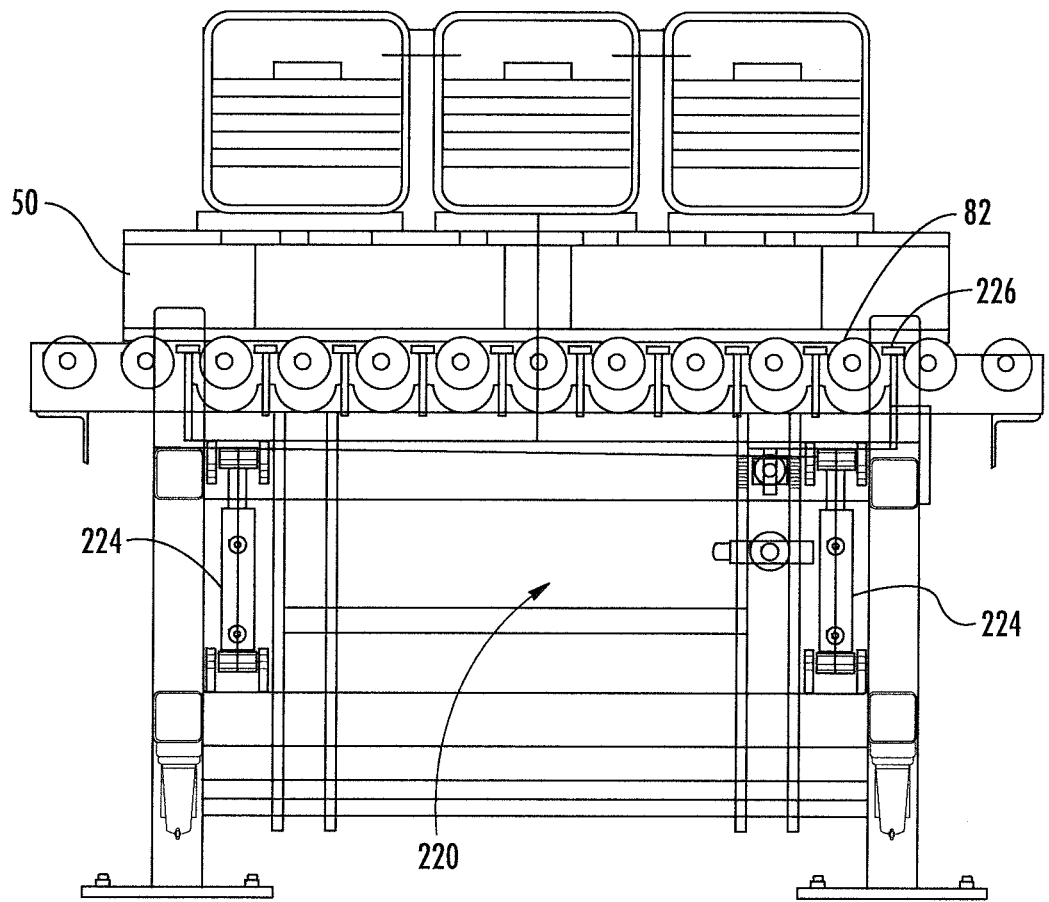
FIG. 17 is an end view of the pallet positioning station illustrated in FIG. 16.
Figure 18:
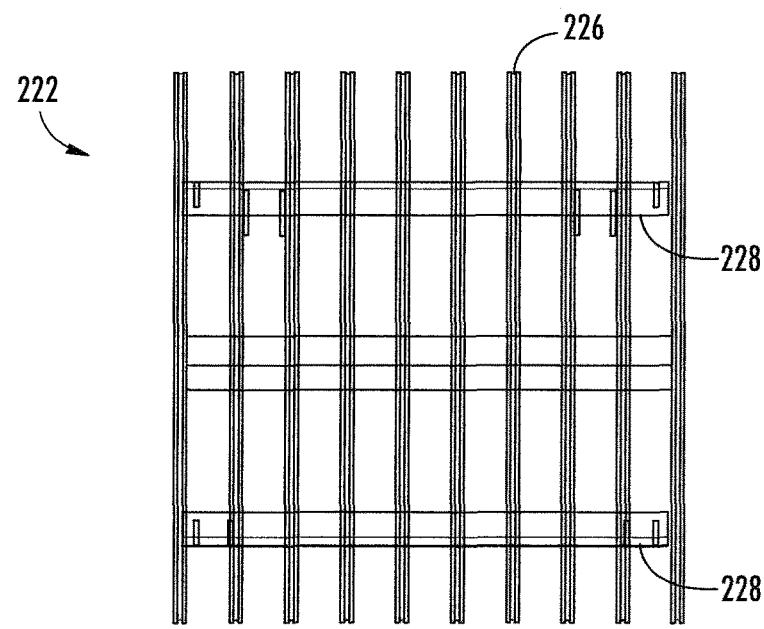
FIG. 18 is a top view of the lifting grate as illustrated in FIG. 17 separated from the roller conveyor.
Figure 19:
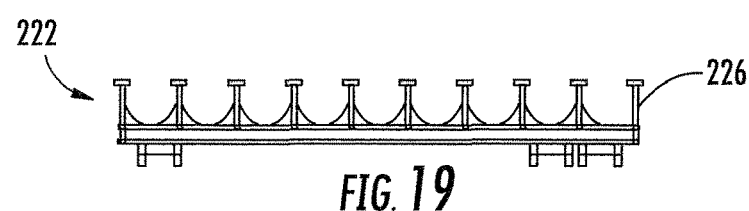
FIG. 19 is an end view of the lifting grate illustrated in FIG. 18.
Figure 20:
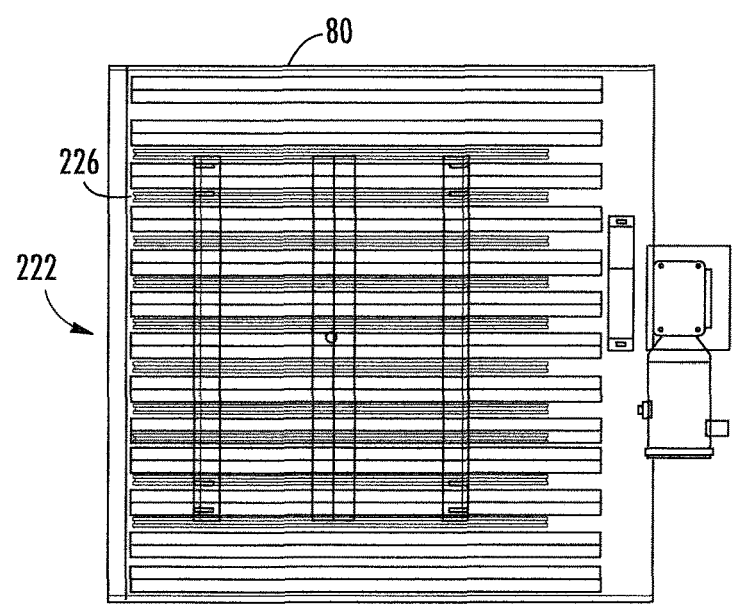
FIG. 20 is a top view of the lifting grate as illustrated in FIG. 17 positioned between the rollers on the roller conveyor with the pallet removed.

When the lift grate 222 is in the retracted position, the vertical actuators 224 are in the retracted positon, as best illustrated in FIGS. 16 and 17. In this position the lift grate 222 is recessed below an upper surface of the roller conveyor 80. This allows the roller conveyor 80 to move the test pallet 50 for initially positioning between the pallet impact station 100 and the pallet positioning station 200.

The lift grate 222 comprises a plurality of spaced apart elongated lift elements 226 that are parallel to one another. Each lift element 226 is sized to fit between two adjacent rollers 82 that are part of the roller conveyor 80. The illustrated lift grate 222 includes 10 lift elements 226, for example.

The lift elements 226 are held in a spaced apart relationship based on frame elements 228 coupled perpendicular to the lift elements 226. The vertical actuators 224 are coupled to the frame elements 228. In one embodiment, a side profile of each lifting element 226 is T-shaped. In other another embodiment, a side profile of each lifting element 226 is I-shaped.

Figure 21:
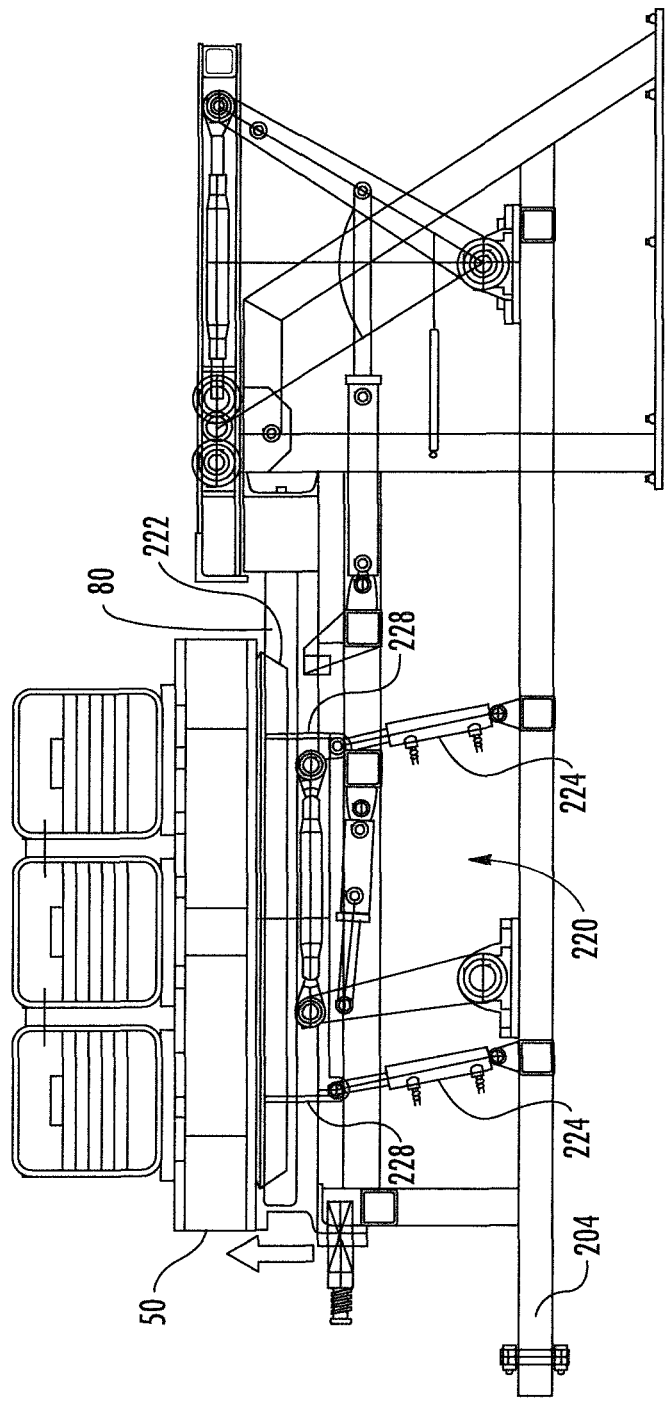
FIG. 21 is a side view of the pallet positioning station illustrated in FIG. 2 with the lifting grate in an extended position.
Figure 22:
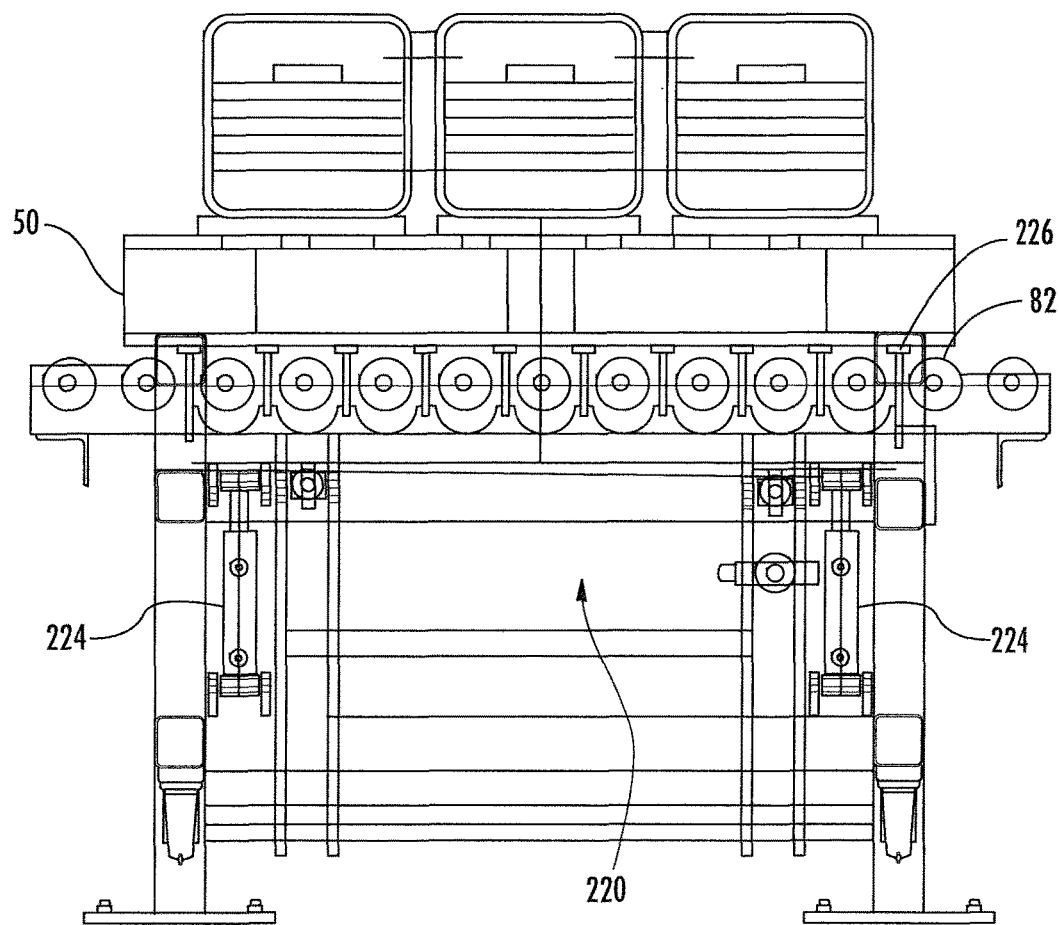
FIG. 22 is an end view of the pallet positioning station illustrated in FIG. 21.

When the vertical actuators 224 are in the extended positon, as illustrated in FIGS. 21 and 22, the lift grate 222 rises above the roller conveyor 80 to lift the test pallet 50 off of the roller conveyor 80. An example lift height of the test pallet 50 is 1 inch above the roller conveyor 80. When the test pallet 50 is lifted off of the roller conveyor 80, this allows the pallet push arm assembly 240 to then move the impact side of the test pallet 50 to the impact reference plane 90.

In addition, the test pallet 50 is impacted by the carriage assembly 110 when lifted off of the roller conveyor 80. This advantageously ensures that the roller conveyor 80 will not cause a drag to be present during impact by the carriage assembly 110. If the test pallet 50 were impacted when on the roller conveyor 80, then a drag may be present if the bearings of the roller conveyor 80 were getting worn, or if any trash or debris gets into the tracks of the roller conveyor 80.

Figure 23:
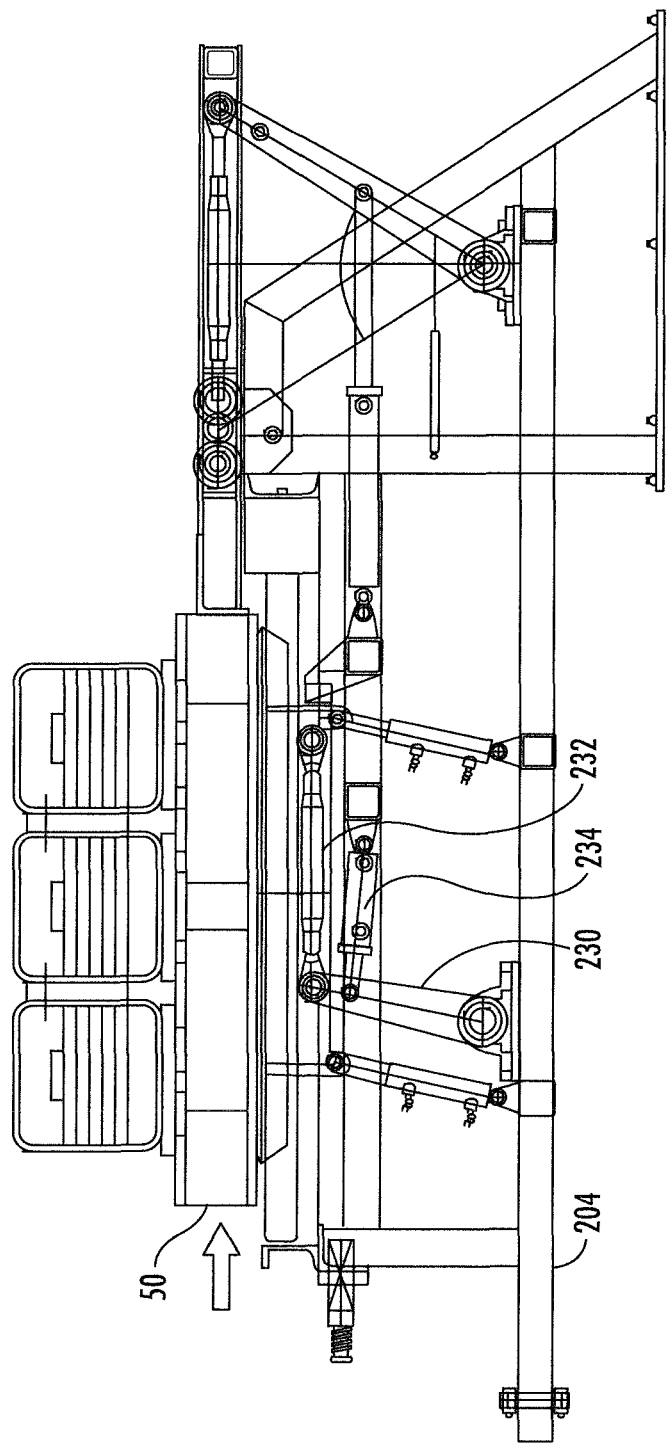
FIG. 23 is a side view of the pallet positioning station illustrated in FIG. 21 with the lifting grate moving the test pallet to be squared with the pallet push arm.

Referring now to FIG. 23, the illustrated pallet lift assembly 220 is further configured to move the lifting grate 222 in a horizontal direction. After the test pallet 50 has been raised off of the roller conveyor 80, the lifting grate 222 is moved towards the pallet push arm 242 so that the test pallet 50 is squared with respect to the pallet push arm 242.

For horizontal movement of the lifting grate 222, the pallet lift assembly 220 further includes a radius arm 230 rotatably coupled to the frame 204 and a link 232 that extends between the radius arm 230 and the lift grate 222. At least one horizontal actuator 234 extends between the frame 204 and the radius arm 230 for moving the lift grate 222 when activated via the controller 150 in a horizontal direction. Each horizontal actuator 224 is a hydraulic actuator, for example, and is controlled by the controller 150.

The controller 150 is configured to operate the vertical actuators 224 and the horizontal actuator 234 simultaneously. Although not illustrated, there are a plurality of sensors associated with the lifting grate 222 to monitor its position. As an alternative to the controller 150 moving the lifting grate in a vertical and/or horizontal direction so as to reposition the test pallet 50, a test operator may manually take over control of the pallet lift assembly to control movement of the lifting grate 222.

Figure 24:
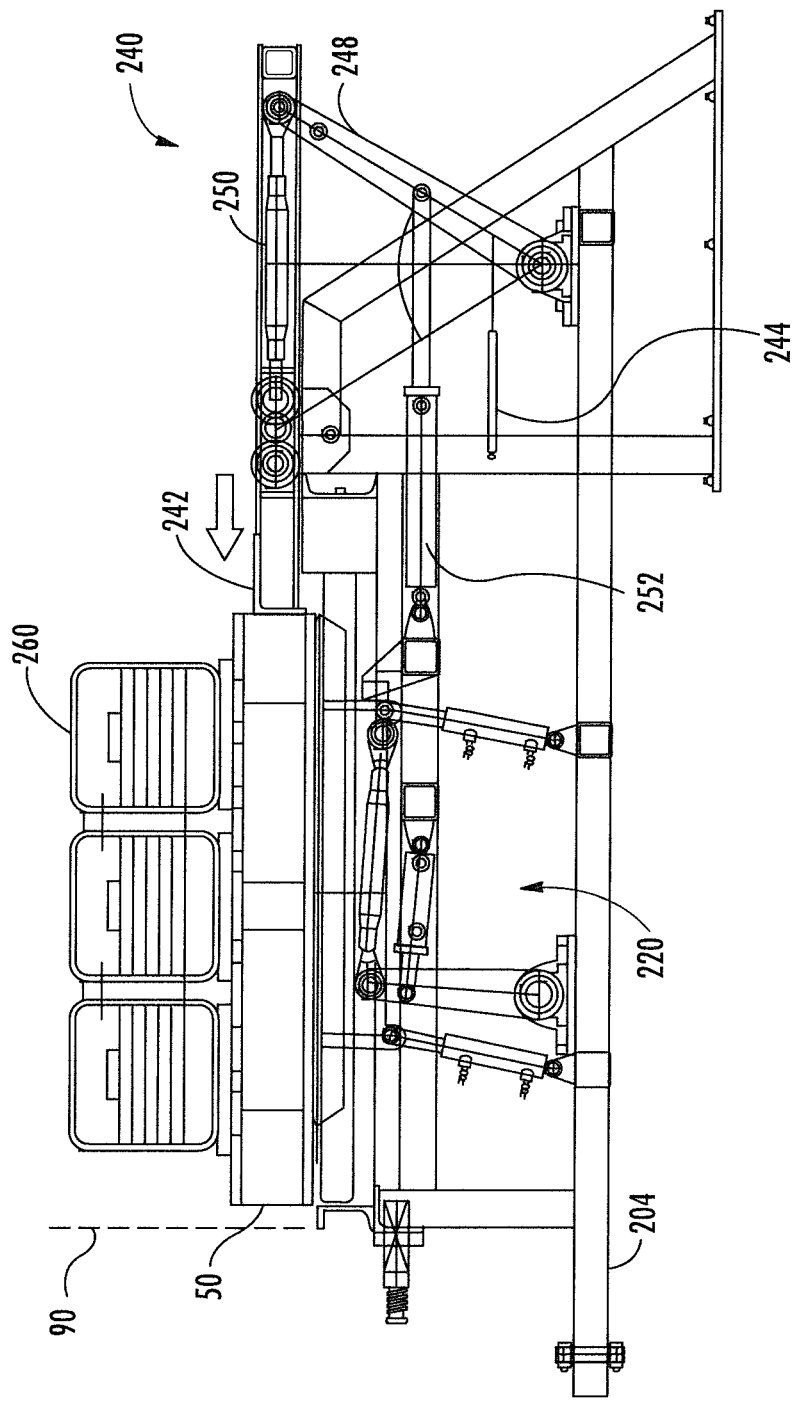
FIG. 24 is a side view of the pallet positioning station illustrated in FIG. 23 with the pallet push arm assembly moving the test pallet towards the impact reference plane.

After the pallet lift assembly 220 has squared the test pallet 50 with the pallet push arm 242, then the pallet push arm assembly 240 is operated by the controller 150 to push the test pallet 50 towards the impact reference plane 90, as illustrated in FIG. 24. The controller 150 knows when the impact side of the test pallet 50 reaches the impact reference plane 90.

The controller 150 receives the size or dimensions of the test pallet 50 prior to repositioning. This information may be stored in an RFID tag 154 carried by the test pallet 50, and communicated to the controller 150 via an RFID reader 152. The controller 150 subtracts the distance to the impact reference plane 90 by the width of the test pallet 50 to determine how far to push the test pallet 50. As the pallet push arm assembly 240 is moving the test pallet 50, the movement sensor 244 provides a distance signal to the controller 150.

As illustrated in the figures, one or more unit loads 260 may be placed on the cargo layer of the test pallet 50. The unit load 260 is to simulate a customer's product being carried by the test pallet 50. The unit loads may vary between 250 to 2500 pounds, for example.

Figure 25:
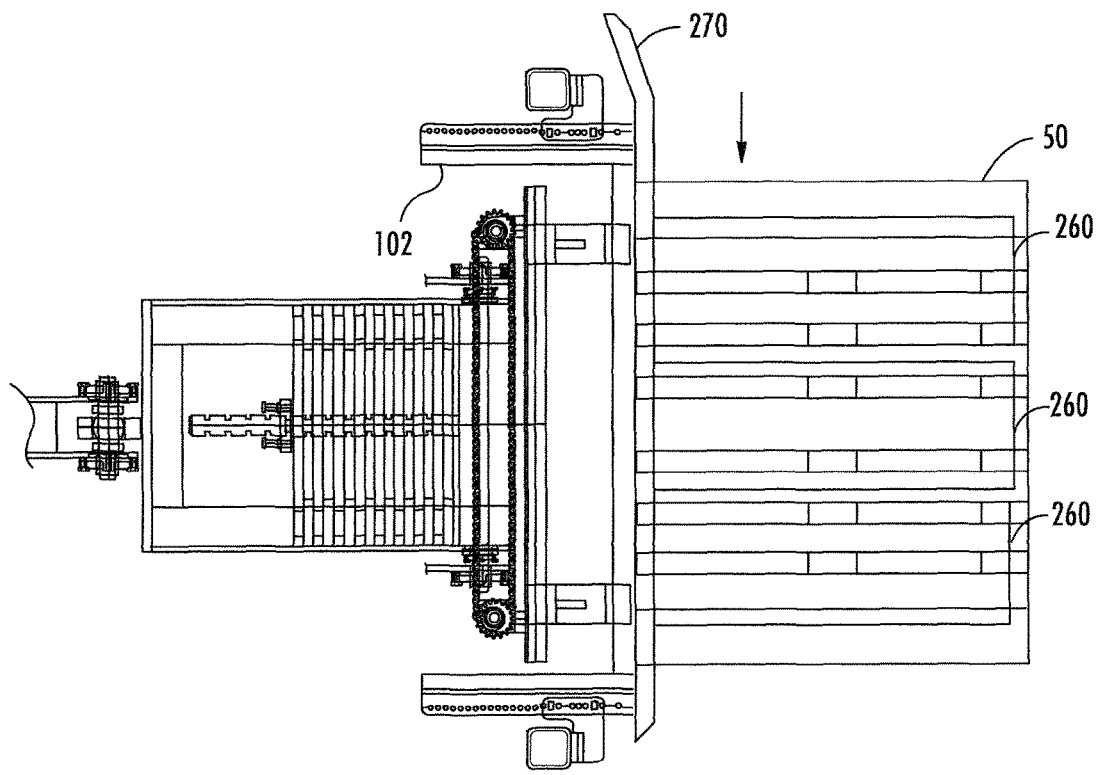
FIG. 25 is a top view of the test pallet with the unit loads thereon in contact with the stationary unit load push bar.
Figure 26:
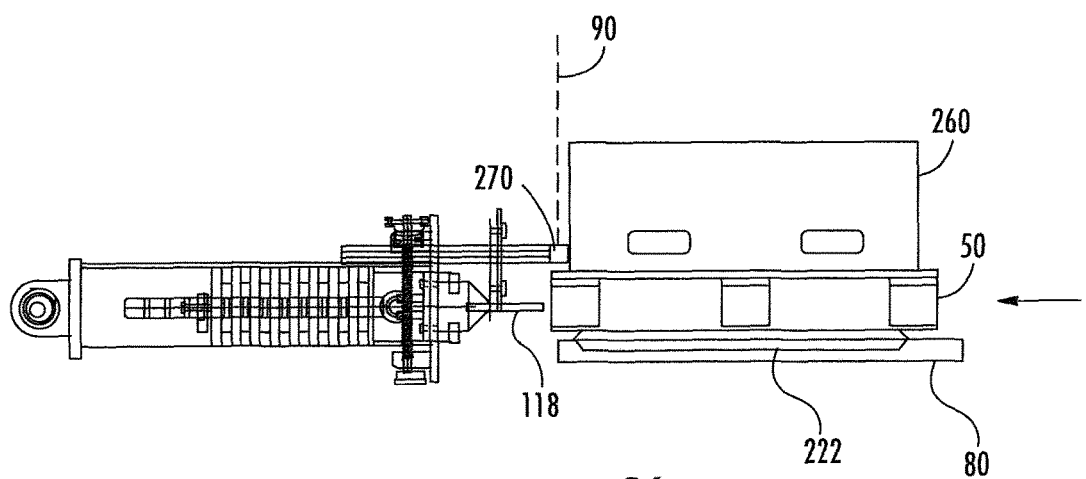
FIG. 26 is a partial side view of the test pallet and unit loads illustrated in FIG. 25.

Prior to impact by the carriage assembly 110, the unit loads 260 on top of the test pallet 50 need to be repositioned. This is accomplished with a stationary unit load push bar 270 coupled to the frame 102 of the pallet impact station 100, as illustrated in FIGS. 25-26.

The stationary unit load push bar 270 is above the height of the test pallet 50, and extends past the impact reference plane 90 so as to make contact with the unit loads 260. As the pallet push arm assembly 240 pushes the impact side of the test pallet 50 towards the impact reference plane 90, the unit loads 260 contact the stationary unit load push bar 270. This results in the unit loads 260 being repositioned on the test pallet 50.

The pallet push arm assembly 240 includes a pair of spaced apart radius arms 248 rotatably coupled to the frame 204, and a pair of respective links 250 extending between the pair of radius arms 248 and the pallet push arm 242. A pair of actuators 252 extend between the pair of radius arms 248 and the pallet push arm 242 for moving the test pallet 50 when activated via the controller 150.

Figure 27:
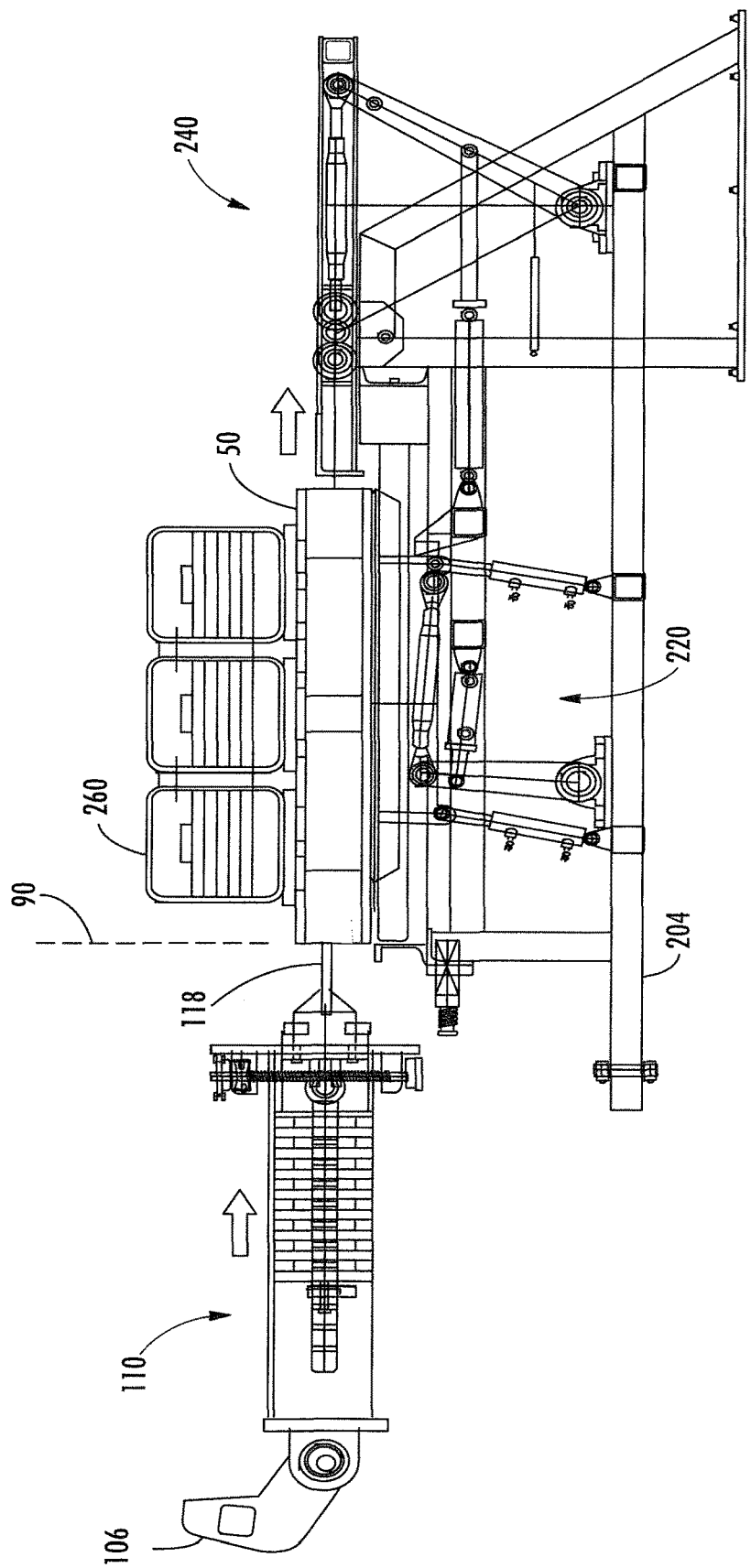
FIG. 27 is a partial side view of the pallet tester with the carriage assembly contacting the test pallet in accordance with the present invention.

After the impact side of the test pallet 50 is aligned with the impact reference plane 90, and the units loads 260 have been repositioned as well, the pallet push arm assembly 240 pulls the pallet push arm 242 away from the test pallet 50, as illustrated in FIG. 27. The pallet push arm 242 is returned back to its zero reference point as determined by the controller 150 reading the signal generated by the movement sensor 244. The test pallet 50 is now ready for impact by the carriage assembly 110.

Figure 28:
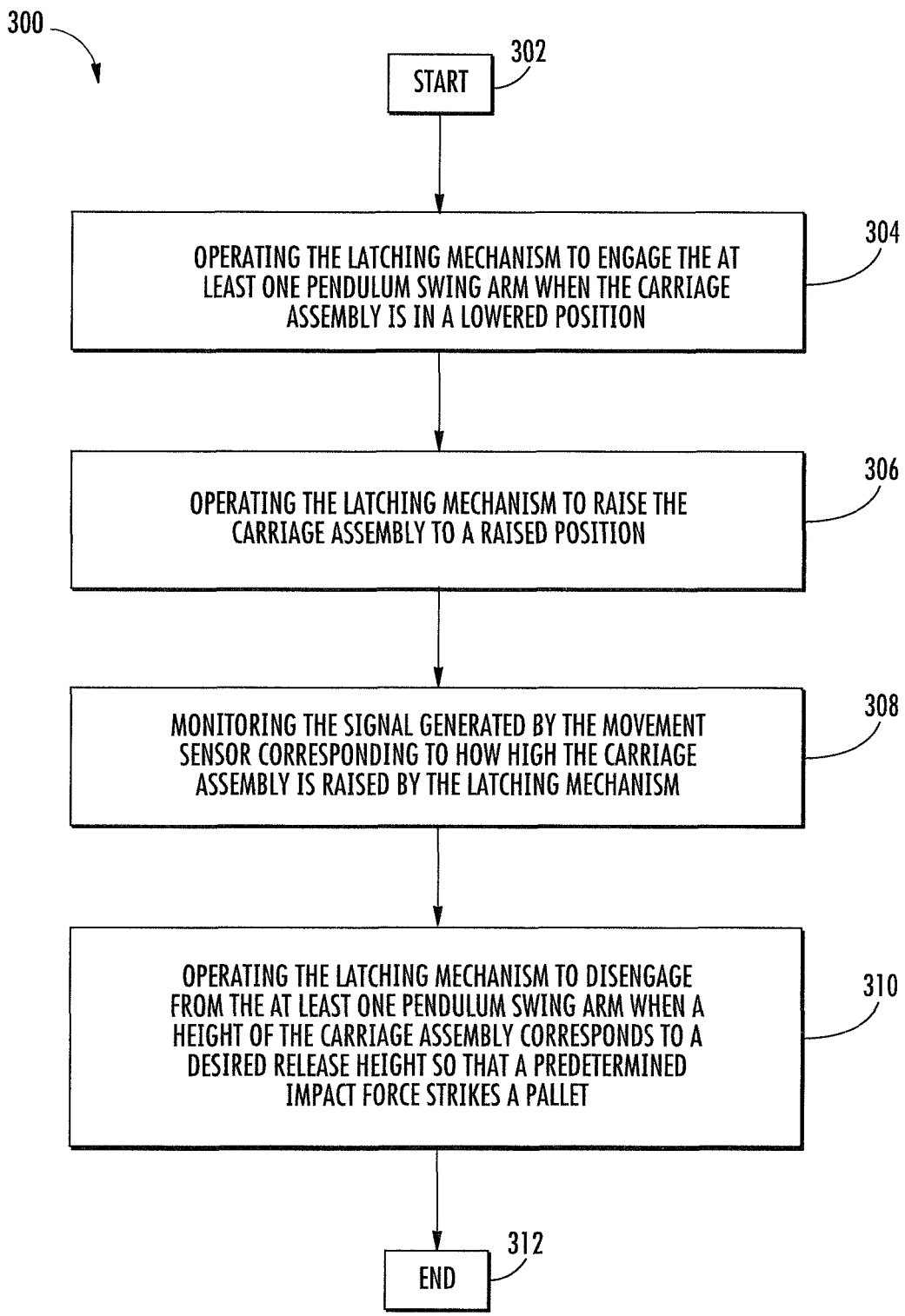
FIG. 28 is a flowchart illustrating a method for operating the pallet impact station illustrated in FIG. 1.

Another aspect is directed to a method for operating the pallet impact station 100, as will now be discussed in reference to the flowchart 300 in FIG. 28. From the start (Block 302), the method includes operating the latching mechanism 120 at Block 304 to engage the at least one pendulum swing arm 106 when the carriage assembly 110 is in a lowered position, and operating the latching mechanism 120 at Block 306 to raise the carriage assembly 110 to a raised positon. The signal generated by the movement sensor 140 corresponding to how high the carriage assembly 110 is raised by the latching mechanism 120 is monitored at Block

308. The method further includes operating the latching mechanism 120 to disengage from the at least one pendulum swing arm 106 at Block 310 when a height of the carriage assembly 110 corresponds to a desired release height so that a predetermined impact force strikes the test pallet 50. The method ends at Block 312.

Figure 29:
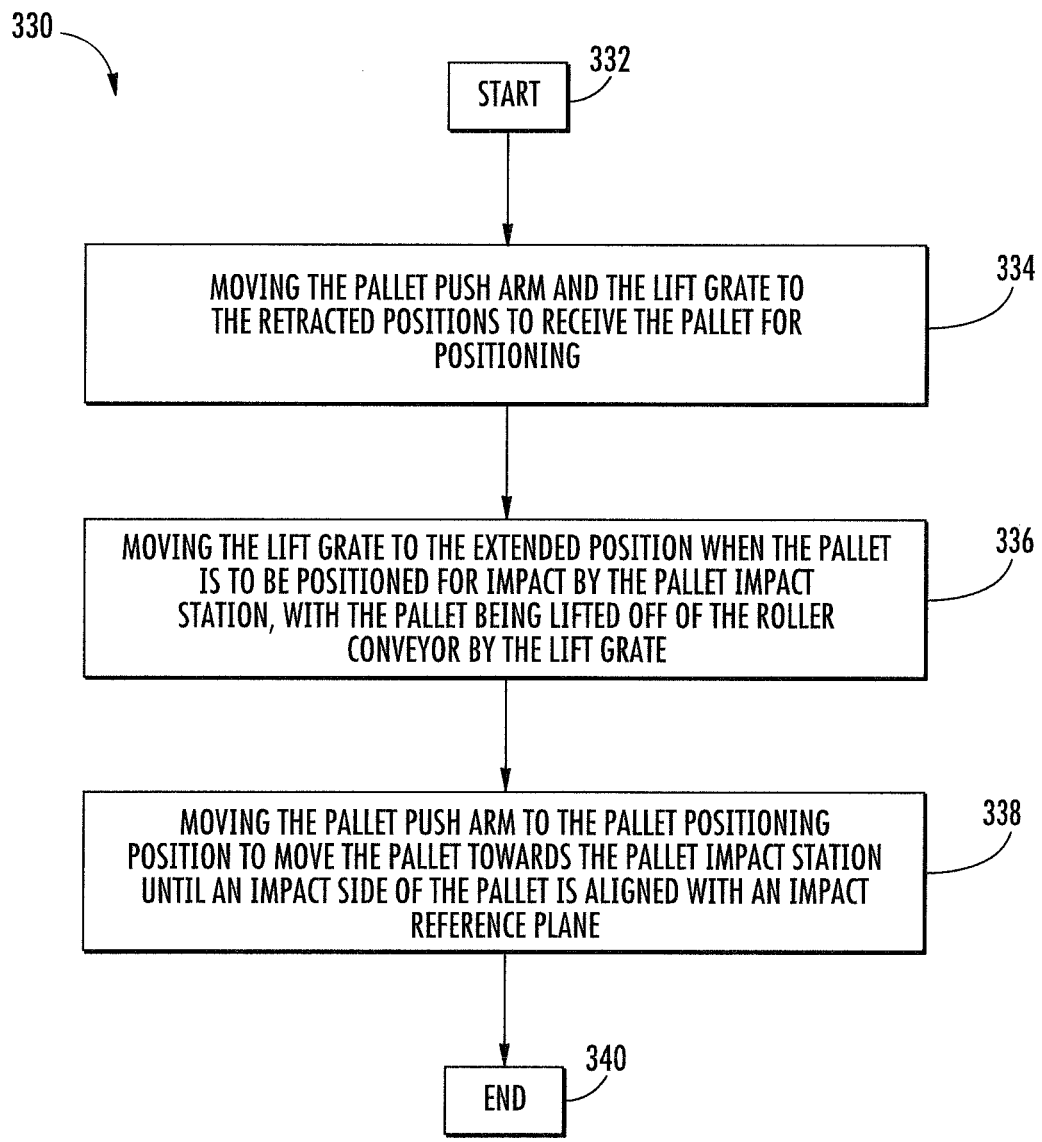
FIG. 29 is a flowchart illustrating a method for operating the pallet positioning station illustrated in FIG. 2.

Another aspect is directed to a method for operating the pallet positioning station 200, as will now be discussed in reference to the flowchart 330 in FIG. 29. From the start (Block 332), the method includes moving the pallet push arm 242 and the lift grate 222 to the retracted positions to receive the test pallet 50 for positioning at Block 334. The lift grate 222 is moved to the extended position at Block 336 when the test pallet 50 is to be positioned for impact by the pallet impact station 100, with the test pallet 50 being lifted off of the roller conveyor 80 by the lift grate 222. The pallet push arm 242 is moved to the pallet positioning position at Block 338 to move the test pallet 50 towards the pallet impact station 100 until an impact side of the test pallet 50 is aligned with an impact reference plane 90. The method ends at Block 340.

Figure 30:
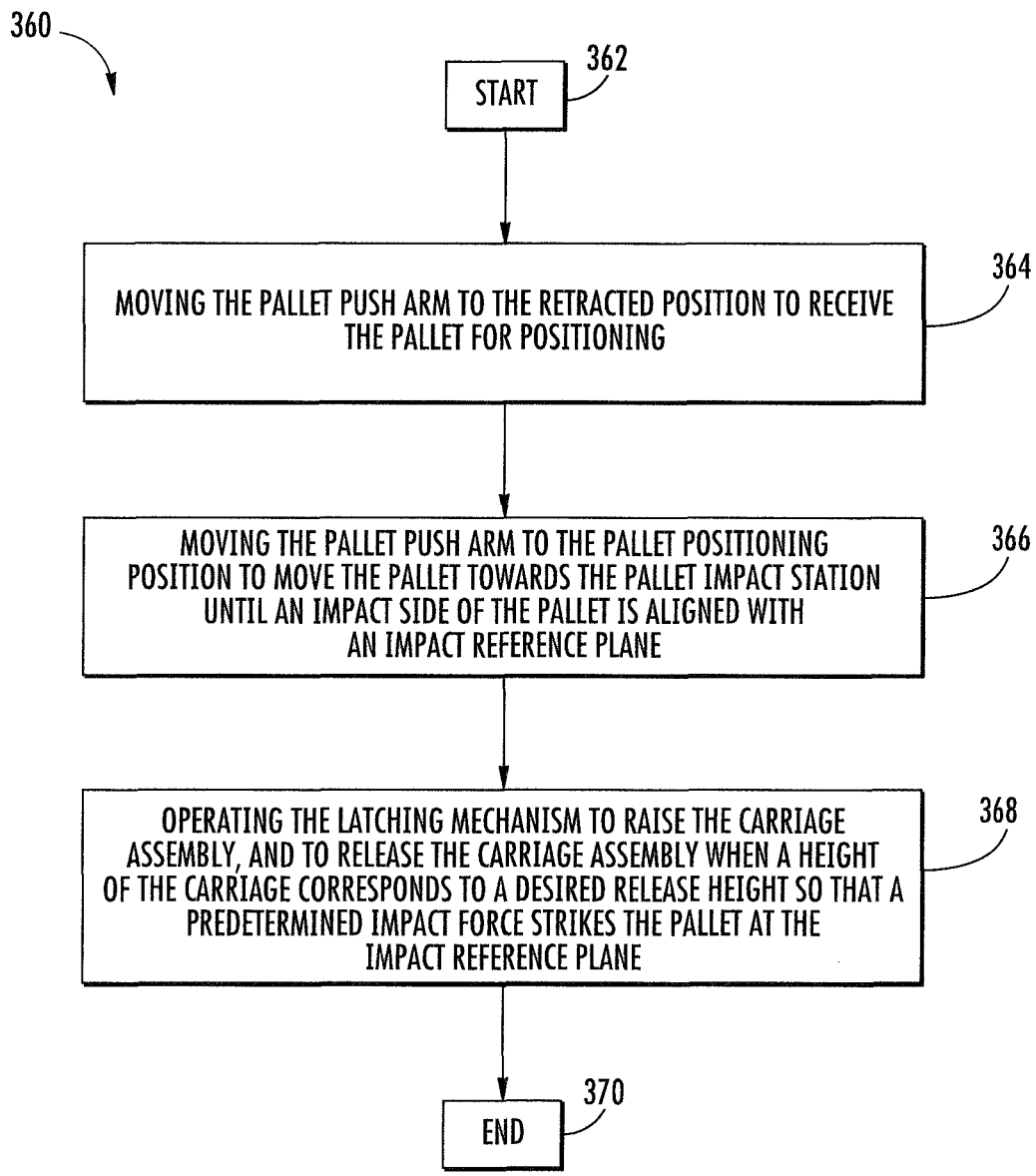
FIG. 30 is a flowchart illustrating a method for testing a pallet using the pallet tester illustrated in FIGS. 1 and 2.

Yet another aspect is directed to a method for testing a pallet 50 using the pallet tester 100, 200, as will now be discussed in reference to the flowchart 360 in FIG. 30. From the start (Block 362), the method includes moving the pallet push arm 242 to the retracted position at Block 364 to receive the pallet 50 for positioning, and moving the pallet push arm 242 to the pallet positioning position at Block 366 to move the pallet 50 towards the pallet impact station 100 until an impact side of the pallet 50 is aligned with an impact reference plane 90. The latching mechanism 120 is operated at Block 368 to raise the carriage assembly 110, and to release the carriage assembly 110 when a height of the carriage assembly 110 corresponds to a desired release height so that a predetermined impact force strikes the pallet 50 at the impact reference plane 90. The method ends at Block 370.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed:

1. A pallet positioning station for positioning a pallet on a roller conveyor to be impacted by a pallet impact station, the pallet positioning station comprising:
   a frame adjacent the roller conveyor and aligned with the pallet impact station;
   a pallet lift assembly carried by said frame and positioned below the roller conveyor, and comprising a lift grate moveable between a retracted position and an extended position, with said lift grate recessed below an upper surface of the roller conveyor when in the retracted position, and with said lift grate extending above the upper surface of the roller conveyor when in the extended position;
   a pallet push arm assembly carried by said frame and comprising a pallet push arm movable between a retracted position and a pallet positioning position; and
   a controller configured to
   move said pallet push arm and said lift grate to the retracted positions to receive the pallet for positioning,
   move said lift grate to the extended position when the pallet is to be positioned for impact by the pallet impact station, with the pallet being lifted off of the roller conveyor by said lift grate, and
   move said pallet push arm to the pallet positioning position to move the pallet towards the pallet impact station until an impact side of the pallet is aligned with an impact reference plane.

2. The pallet positioning station according to claim 1 further comprising a movement sensor carried by said frame and configured to generate a signal corresponding to movement of said pallet push arm when in the pallet positioning position; and wherein said controller is further configured to move said pallet push arm in the pallet positioning position until the generated signal reaches a predetermined value, with the predetermined value corresponding to when the impact side of the pallet is aligned with the impact reference plane.

3. The pallet positioning station according to claim 1 wherein said controller is further configured to move said pallet push arm back to the retracted position after the impact side of the pallet is aligned with the impact reference plane.

4. The pallet positioning station according to claim 1 wherein the roller conveyor comprises a plurality of spaced apart elongated rollers that are parallel to one another; and wherein said lift grate comprises a plurality of spaced apart elongated lift elements, with each respective lift element sized to fit between two adjacent rollers.

5. The pallet positioning station according to claim 1 wherein said pallet lift assembly further comprises a plurality of vertical actuators extending between said frame and said lift grate for moving said lift grate when activated via said controller between the retracted position and the extended position.

6. The pallet positioning station according to claim 5 wherein said pallet lift assembly further comprises at least one horizontal actuator for moving said lift grate in a horizontal direction between the impact reference plane and said pallet push arm; and wherein said controller is further configured to move said lift grate in the horizontal direction towards the pallet push arm so that the pallet contacts said pallet push arm before said pallet push arm is moved to the pallet positioning position.

7. The pallet positioning station according to claim 6 wherein said pallet lift assembly further comprises:
   a radius arm rotatably coupled to said frame; and
   a link extending between said radius arm and said lift grate;
   with said at least one horizontal actuator extending between said frame and said radius arm.

8. The pallet positioning station according to claim 6 wherein said controller is further configured to operate said plurality of vertical actuators and said at least one horizontal actuator simultaneously.

9. The pallet positioning station according to claim 6 wherein said plurality of vertical actuators and said at least one horizontal actuator each comprises a hydraulic actuator.

10. The pallet positioning station according to claim 1 wherein said pallet push arm assembly comprises:
    a pair of spaced apart radius arms rotatably coupled to said frame;
    a pair of spaced apart links extending between said pair of radius arms and said pallet push arm; and
    a pair of actuators extending between said frame and said pair of radius arms for moving the pallet when activated via said controller.

11. The pallet positioning station according to claim 10 wherein said movement sensor comprises a linear variable differential transformer (LVDT) extending between said frame and one of said radius arms.

12. The pallet positioning station according to claim 1 wherein the pallet carries a unit load during impact with the pallet impact station; wherein the pallet impact station comprises a stationary unit load push bar positioned above the roller conveyor and adjacent the impact reference plane; and as said controller moves said pallet push arm in the pallet positioning position to move the pallet, the unit load contacts the stationary unit load push bar as the impact side of the pallet continues to move towards the impact reference plane.

13. A pallet positioning station for positioning a pallet on a roller conveyor to be impacted by a pallet impact station, with the roller conveyor initially positioning the pallet adjacent the pallet impact station, the pallet positioning station comprising:
- a frame adjacent the roller conveyor and aligned with the pallet impact station;
- a pallet lift assembly carried by said frame and positioned below the roller conveyor, and comprising a lift grate moveable between a retracted position and an extended position, with said lift grate recessed below an upper surface of the roller conveyor when in the retracted position, and with said lift grate extending above the upper surface of the roller conveyor when in the extended position;
- a pallet push arm assembly carried by said frame and comprising a pallet push arm movable between a retracted position and a pallet positioning position;
- a movement sensor carried by said frame and configured to generate a signal corresponding to movement of said pallet push arm when in the pallet positioning position; and
- a controller configured to
  - move said pallet push arm and said lift grate to the retracted positions to receive the pallet for positioning,
  - move said lift grate to the extended position when the pallet is to be positioned for impact by the pallet impact station, with the pallet being lifted off of the roller conveyor by said lift grate, and
  - move said pallet push arm to the pallet positioning position to move the pallet towards the pallet impact station until an impact side of the pallet is aligned with an impact reference plane based on the generated signal reaching a predetermined value, with the predetermined value corresponding to when the impact side of the pallet is aligned with the impact reference plane.

14. The pallet positioning station according to claim 13 wherein said controller is further configured to move said pallet push arm back to the retracted position after the impact side of the pallet is aligned with the impact reference plane.

15. The pallet positioning station according to claim 13 wherein the roller conveyor comprises a plurality of spaced apart elongated rollers that are parallel to one another; and wherein said lift grate comprises a plurality of spaced apart elongated lift elements, with each respective lift element sized to fit between two adjacent rollers.

16. The pallet positioning station according to claim 13 wherein said pallet lift assembly further comprises a plurality of vertical actuators extending between said frame and said lift grate for moving said lift grate when activated via said controller between the retracted position and the extended position.

17. The pallet positioning station according to claim 16 wherein said pallet lift assembly further comprises at least one horizontal actuator for moving said lift grate in a horizontal direction between the impact reference plane and said pallet push arm; and wherein said controller is further configured to move said lift grate in the horizontal direction towards the pallet push arm so that the pallet contacts said pallet push arm before said pallet push arm is moved to the pallet positioning position.

18. The pallet positioning station according to claim 16 wherein said controller is further configured to operate said plurality of vertical actuators and said at least one horizontal actuator simultaneously.

* * * * *